US011492381B2

(12) United States Patent
Galgiani et al.

(10) Patent No.: US 11,492,381 B2
(45) Date of Patent: Nov. 8, 2022

(54) QUANTITATIVE ENZYME-LINKED IMMUNOASSAY (ELISA) TO APPROXIMATE COMPLEMENT FIXING ANTIBODY TITERS IN SERUM FROM PATIENTS WITH COCCIDIOIDOMYCOSIS

(71) Applicant: ARIZONA BOARD OF REGENTS ON BEHALF OF THE UNIVERSITY OF ARIZONA, Tucson, AZ (US)

(72) Inventors: John N. Galgiani, Tucson, AZ (US); Michael D. L. Johnson, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 70 days.

(21) Appl. No.: 17/023,133

(22) Filed: Sep. 16, 2020

(65) Prior Publication Data

US 2021/0009642 A1 Jan. 14, 2021

Related U.S. Application Data

(63) Continuation-in-part of application No. 16/058,538, filed on Aug. 8, 2018, now abandoned.

(60) Provisional application No. 62/542,594, filed on Aug. 8, 2017.

(51) Int. Cl.
*C07K 14/37* (2006.01)
*G01N 33/68* (2006.01)
*G01N 33/543* (2006.01)

(52) U.S. Cl.
CPC ....... *C07K 14/37* (2013.01); *G01N 33/54366* (2013.01); *G01N 33/6854* (2013.01); *G01N 2333/37* (2013.01); *G01N 2800/26* (2013.01)

(58) Field of Classification Search
CPC ............... C07K 14/37; G01N 33/6854; G01N 33/54366; G01N 2333/37; G01N 2800/26
See application file for complete search history.

(56) References Cited

PUBLICATIONS

Sharpton et al. 2009 (Comparative genomic analyses of the human fungal pathogens Coccidioides and their relatives; Genome Research 19:1722-1731). (Year: 2009).*
Durkin et al. 2008 (Diagnosis of Coccidioidomycosis with Use of the Coccidioides Antigen Enzyme Immunoassay; Clin. Infectious Diseases 47: 69-73). (Year: 2008).*
Yang et al. Mapping of a Coccidioides immitis-Specific Epitope That Reacts with Complement-Fixing Antibody. Infection and Immunity, Oct. 1997, p. 4068-4074 vol. 65, No. 10.
Sano et al. 2006 (Reexamination of *Coccidioides* spp. Reserved in the Research Center for Pathogenic Fungi and Microbial Toxicoses, Chiba University, Based on a Multiple Gene Analysis; Jpn. J. Med. Mycol. 47: 113-117) (Year 2006).
Johnson et al. 1992 (The Coccidioidal Complement Fixation and Immunodiffusion-Complement Antigen Is a Chitinase; Infection and Immunity, 60(7):2588-2592). (Year: 1992).
Johnson et al. 1993 (Amino-Terminal Sequence Analysis of the Coccidioides Chitinase/ Immunodiffusion-Complement Fixation Protein; Infection and Immunity 61(7): 2588-2592). (Year: 1993).

* cited by examiner

*Primary Examiner* — Mary Maille Lyons
(74) *Attorney, Agent, or Firm* — Nguyen Tarbet LLC

(57) ABSTRACT

Coccidioidomycosis is most often diagnosed serologically and the quantitative complement-fixing antibody test (CF) is considered prognostically useful. Because CF is complex, labor-intensive, and poorly standardized, an enzyme-linked immunoassay (ELISA) alternative would be attractive. The present invention features an antibody-binding domain that is restricted to a 200 amino acid recombinant peptide of the known antigen responsible for CF activity. Overlapping truncations of this peptide do not bind CF antibodies, suggesting that the responsible epitope(s) are conformational. Further, anchoring the antigenic peptide to the ELISA plate by means of a C-terminal tag instead of allowing the peptide to randomly adhere to the plastic plate improves sensitivity of antibody detection by one to two logs in different sera. The newly developed ELISA shows a significant quantitative correlation with CF. This ELISA shows potential as the basis for a new quantitative assay for coccidioidal antibodies.

2 Claims, 6 Drawing Sheets

Specification includes a Sequence Listing.

EIA versus IDCF

All CF antibodies bind $CST1_{111-310}$

* No cleavage from vector's maltose binding protein (MBP), MW=43.5kDa, for keeping the Subunits soluble.

SEQUENCE LISTING

```
<160> NUMBER OF SEQ ID NOS: 27

<210> SEQ ID NO 1
<211> LENGTH: 427
<212> TYPE: PRT
<213> ORGANISM: Unknown
<220> FEATURE:
<223> OTHER INFORMATION: Coccidioides posadasii

<400> SEQUENCE: 1

Met Arg Phe Leu Ile Gly Ala Leu Leu Thr Leu Gln Thr Leu Val Gln
1               5                   10                  15

Ala Ser Ser Met Ser Ser Met Pro Asn Tyr Tyr Pro Val Pro Glu Ala
            20                  25                  30
```

-continued

```
Pro Ala Glu Gly Gly Phe Arg Ser Val Val Tyr Phe Val Asn Trp Ala
        35                  40                  45

Ile Tyr Gly Arg Gly His Asn Pro Gln Asp Leu Lys Ala Asp Gln Phe
    50                  55                  60

Thr His Ile Leu Tyr Ala Phe Ala Asn Ile Arg Pro Ser Gly Glu Val
65                  70                  75                  80

Tyr Leu Ser Asp Thr Trp Ala Asp Thr Asp Lys His Tyr Pro Gly Asp
                85                  90                  95

Lys Trp Asp Glu Pro Gly Asn Asn Val Tyr Gly Cys Ile Lys Gln Met
            100                 105                 110

Tyr Leu Leu Lys Lys Asn Asn Arg Asn Leu Lys Thr Leu Leu Ser Ile
        115                 120                 125

Gly Gly Trp Thr Tyr Ser Pro Asn Phe Lys Thr Pro Ala Ser Thr Glu
    130                 135                 140

Glu Gly Arg Lys Lys Phe Ala Asp Thr Ser Leu Lys Leu Met Lys Asp
145                 150                 155                 160

Leu Gly Phe Asp Gly Ile Asp Ile Asp Trp Glu Tyr Pro Glu Asp Glu
                165                 170                 175

Lys Gln Ala Asn Asp Phe Val Leu Leu Leu Lys Ala Cys Arg Glu Ala
            180                 185                 190

Leu Asp Ala Tyr Ser Ala Lys His Pro Asn Gly Lys Lys Phe Leu Leu
        195                 200                 205

Thr Ile Ala Ser Pro Ala Gly Pro Gln Asn Tyr Asn Lys Leu Lys Leu
    210                 215                 220

Ala Glu Met Asp Lys Tyr Leu Asp Phe Trp Asn Leu Met Ala Tyr Asp
225                 230                 235                 240

Phe Ser Gly Ser Trp Asp Lys Val Ser Gly His Met Ser Asn Val Phe
                245                 250                 255

Pro Ser Thr Thr Lys Pro Glu Ser Thr Pro Phe Ser Ser Asp Lys Ala
            260                 265                 270

Val Lys Asp Tyr Ile Lys Ala Gly Val Pro Ala Asn Lys Ile Val Leu
        275                 280                 285

Gly Met Pro Leu Tyr Gly Arg Ala Phe Ala Ser Thr Asp Gly Ile Gly
    290                 295                 300

Thr Ser Phe Asn Gly Val Gly Gly Gly Ser Trp Glu Asn Gly Val Trp
305                 310                 315                 320

Asp Tyr Lys Asp Met Pro Gln Gln Gly Ala Gln Val Thr Glu Leu Glu
                325                 330                 335

Asp Ile Ala Ala Ser Tyr Ser Tyr Asp Lys Asn Lys Arg Tyr Leu Ile
            340                 345                 350

Ser Tyr Asp Thr Val Lys Ile Ala Gly Lys Lys Ala Glu Tyr Ile Thr
        355                 360                 365

Lys Asn Gly Met Gly Gly Gly Met Trp Trp Glu Ser Ser Ser Asp Lys
    370                 375                 380

Thr Gly Asn Glu Ser Leu Val Gly Thr Val Val Asn Gly Leu Gly Gly
385                 390                 395                 400

Thr Gly Lys Leu Glu Gln Arg Glu Asn Glu Leu Ser Tyr Pro Glu Ser
                405                 410                 415

Val Tyr Asp Asn Leu Lys Asn Gly Met Pro Ser
            420                 425
```

<210> SEQ ID NO 2
<211> LENGTH: 291

-continued

<212> TYPE: PRT
<213> ORGANISM: Unknown
<220> FEATURE:
<223> OTHER INFORMATION: Amino acids 20-310 of Cts1 (Coccidioides posadiasii, GenBank AAA92643.1)

<400> SEQUENCE: 2

```
Met Ser Ser Met Pro Asn Tyr Tyr Pro Val Pro Glu Ala Pro Ala Glu
1               5                   10                  15

Gly Gly Phe Arg Ser Val Val Tyr Phe Val Asn Trp Ala Ile Tyr Gly
            20                  25                  30

Arg Gly His Asn Pro Gln Asp Leu Lys Ala Asp Gln Phe Thr His Ile
        35                  40                  45

Leu Tyr Ala Phe Ala Asn Ile Arg Pro Ser Gly Glu Val Tyr Leu Ser
    50                  55                  60

Asp Thr Trp Ala Asp Thr Asp Lys His Tyr Pro Gly Asp Lys Trp Asp
65                  70                  75                  80

Glu Pro Gly Asn Asn Val Tyr Gly Cys Ile Lys Gln Met Tyr Leu Leu
                85                  90                  95

Lys Lys Asn Asn Arg Asn Leu Lys Thr Leu Leu Ser Ile Gly Gly Trp
            100                 105                 110

Thr Tyr Ser Pro Asn Phe Lys Thr Pro Ala Ser Thr Glu Glu Gly Arg
        115                 120                 125

Lys Lys Phe Ala Asp Thr Ser Leu Lys Leu Met Lys Asp Leu Gly Phe
    130                 135                 140

Asp Gly Ile Asp Ile Asp Trp Glu Tyr Pro Glu Asp Glu Lys Gln Ala
145                 150                 155                 160

Asn Asp Phe Val Leu Leu Leu Lys Ala Cys Arg Glu Ala Leu Asp Ala
                165                 170                 175

Tyr Ser Ala Lys His Pro Asn Gly Lys Lys Phe Leu Leu Thr Ile Ala
            180                 185                 190

Ser Pro Ala Gly Pro Gln Asn Tyr Asn Lys Leu Lys Leu Ala Glu Met
        195                 200                 205

Asp Lys Tyr Leu Asp Phe Trp Asn Leu Met Ala Tyr Asp Phe Ser Gly
    210                 215                 220

Ser Trp Asp Lys Val Ser Gly His Met Ser Asn Val Phe Pro Ser Thr
225                 230                 235                 240

Thr Lys Pro Glu Ser Thr Pro Phe Ser Ser Asp Lys Ala Val Lys Asp
                245                 250                 255

Tyr Ile Lys Ala Gly Val Pro Ala Asn Lys Ile Val Leu Gly Met Pro
            260                 265                 270

Leu Tyr Gly Arg Ala Phe Ala Ser Thr Asp Gly Ile Gly Thr Ser Phe
        275                 280                 285

Asn Gly Val
    290
```

<210> SEQ ID NO 3
<211> LENGTH: 200
<212> TYPE: PRT
<213> ORGANISM: Artificial Sequence
<220> FEATURE:
<223> OTHER INFORMATION: Amino acids 111-310 of Cts1 (Coccidioides posadiasii, GenBank AAA92643.1)

<400> SEQUENCE: 3

```
Gln Met Tyr Leu Leu Lys Lys Asn Asn Arg Asn Leu Lys Thr Leu Leu
1               5                   10                  15
```

-continued

Ser Ile Gly Gly Trp Thr Tyr Ser Pro Asn Phe Lys Thr Pro Ala Ser
            20                  25                  30

Thr Glu Glu Gly Arg Lys Lys Phe Ala Asp Thr Ser Leu Lys Leu Met
        35                  40                  45

Lys Asp Leu Gly Phe Asp Gly Ile Asp Ile Asp Trp Glu Tyr Pro Glu
    50                  55                  60

Asp Glu Lys Gln Ala Asn Asp Phe Val Leu Leu Leu Lys Ala Cys Arg
65                  70                  75                  80

Glu Ala Leu Asp Ala Tyr Ser Ala Lys His Pro Asn Gly Lys Lys Phe
                85                  90                  95

Leu Leu Thr Ile Ala Ser Pro Ala Gly Pro Gln Asn Tyr Asn Lys Leu
            100                 105                 110

Lys Leu Ala Glu Met Asp Lys Tyr Leu Asp Phe Trp Asn Leu Met Ala
        115                 120                 125

Tyr Asp Phe Ser Gly Ser Trp Asp Lys Val Ser Gly His Met Ser Asn
    130                 135                 140

Val Phe Pro Ser Thr Thr Lys Pro Glu Ser Thr Pro Phe Ser Ser Asp
145                 150                 155                 160

Lys Ala Val Lys Asp Tyr Ile Lys Ala Gly Val Pro Ala Asn Lys Ile
                165                 170                 175

Val Leu Gly Met Pro Leu Tyr Gly Arg Ala Phe Ala Ser Thr Asp Gly
            180                 185                 190

Ile Gly Thr Ser Phe Asn Gly Val
        195                 200

<210> SEQ ID NO 4
<211> LENGTH: 206
<212> TYPE: PRT
<213> ORGANISM: Unknown
<220> FEATURE:
<223> OTHER INFORMATION: Amino acids 105-310 of Cts1 (Coccidioides
      posadiasii, GenBank AAA92643.1)

<400> SEQUENCE: 4

Val Tyr Gly Cys Ile Lys Gln Met Tyr Leu Leu Lys Lys Asn Asn Arg
1               5                   10                  15

Asn Leu Lys Thr Leu Leu Ser Ile Gly Gly Trp Thr Tyr Ser Pro Asn
            20                  25                  30

Phe Lys Thr Pro Ala Ser Thr Glu Glu Gly Arg Lys Lys Phe Ala Asp
        35                  40                  45

Thr Ser Leu Lys Leu Met Lys Asp Leu Gly Phe Asp Gly Ile Asp Ile
    50                  55                  60

Asp Trp Glu Tyr Pro Glu Asp Glu Lys Gln Ala Asn Asp Phe Val Leu
65                  70                  75                  80

Leu Leu Lys Ala Cys Arg Glu Ala Leu Asp Ala Tyr Ser Ala Lys His
                85                  90                  95

Pro Asn Gly Lys Lys Phe Leu Leu Thr Ile Ala Ser Pro Ala Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Gly His Met Ser Asn Val Phe Pro Ser Thr Thr Lys Pro Glu Ser
145                 150                 155                 160

Thr Pro Phe Ser Ser Asp Lys Ala Val Lys Asp Tyr Ile Lys Ala Gly
                165                 170                 175

```
Val Pro Ala Asn Lys Ile Val Leu Gly Met Pro Leu Tyr Gly Arg Ala
            180                 185                 190

Phe Ala Ser Thr Asp Gly Ile Gly Thr Ser Phe Asn Gly Val
        195                 200                 205


<210> SEQ ID NO 5
<211> LENGTH: 206
<212> TYPE: PRT
<213> ORGANISM: Unknown
<220> FEATURE:
<223> OTHER INFORMATION: Amino acids 105-310 of Cts1 (Coccidioides
      posadiasii, GenBank AAA92643.1), with L193V and L208V
      substitutions.

<400> SEQUENCE: 5

Val Tyr Gly Cys Ile Lys Gln Met Tyr Leu Leu Lys Lys Asn Asn Arg
1               5                   10                  15

Asn Leu Lys Thr Leu Leu Ser Ile Gly Gly Trp Thr Tyr Ser Pro Asn
            20                  25                  30

Phe Lys Thr Pro Ala Ser Thr Glu Glu Gly Arg Lys Lys Phe Ala Asp
        35                  40                  45

Thr Ser Leu Lys Leu Met Lys Asp Leu Gly Phe Asp Gly Ile Asp Ile
    50                  55                  60

Asp Trp Glu Tyr Pro Glu Asp Glu Lys Gln Ala Asn Asp Phe Val Leu
65                  70                  75                  80

Leu Leu Lys Ala Cys Arg Glu Ala Val Asp Ala Tyr Ser Ala Lys His
                85                  90                  95

Pro Asn Gly Lys Lys Phe Leu Val Thr Ile Ala Ser Pro Ala Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Gly His Met Ser Asn Val Phe Pro Ser Thr Thr Lys Pro Glu Ser
145                 150                 155                 160

Thr Pro Phe Ser Ser Asp Lys Ala Val Lys Asp Tyr Ile Lys Ala Gly
                165                 170                 175

Val Pro Ala Asn Lys Ile Val Leu Gly Met Pro Leu Tyr Gly Arg Ala
            180                 185                 190

Phe Ala Ser Thr Asp Gly Ile Gly Thr Ser Phe Asn Gly Val
        195                 200                 205


<210> SEQ ID NO 6
<211> LENGTH: 206
<212> TYPE: PRT
<213> ORGANISM: Artificial Sequence
<220> FEATURE:
<223> OTHER INFORMATION: Amino acids 105-310 of Cts1 (Coccidioides
      posadiasii, GenBank AAA92643.1), with A151L and E174D
      substitutions.

<400> SEQUENCE: 6

Val Tyr Gly Cys Ile Lys Gln Met Tyr Leu Leu Lys Lys Asn Asn Arg
1               5                   10                  15

Asn Leu Lys Thr Leu Leu Ser Ile Gly Gly Trp Thr Tyr Ser Pro Asn
            20                  25                  30

Phe Lys Thr Pro Ala Ser Thr Glu Glu Gly Arg Lys Lys Phe Leu Asp
        35                  40                  45
```

-continued

```
Thr Ser Leu Lys Leu Met Lys Asp Leu Gly Phe Asp Gly Ile Asp Ile
    50                  55                  60

Asp Trp Glu Tyr Pro Asp Asp Glu Lys Gln Ala Asn Asp Phe Val Leu
65                  70                  75                  80

Leu Leu Lys Ala Cys Arg Glu Ala Leu Asp Ala Tyr Ser Ala Lys His
                85                  90                  95

Pro Asn Gly Lys Lys Phe Leu Leu Thr Ile Ala Ser Pro Ala Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Gly His Met Ser Asn Val Phe Pro Ser Thr Thr Lys Pro Glu Ser
145                 150                 155                 160

Thr Pro Phe Ser Ser Asp Lys Ala Val Lys Asp Tyr Ile Lys Ala Gly
                165                 170                 175

Val Pro Ala Asn Lys Ile Val Leu Gly Met Pro Leu Tyr Gly Arg Ala
            180                 185                 190

Phe Ala Ser Thr Asp Gly Ile Gly Thr Ser Phe Asn Gly Val
        195                 200                 205


<210> SEQ ID NO 7
<211> LENGTH: 206
<212> TYPE: PRT
<213> ORGANISM: Artificial Sequence
<220> FEATURE:
<223> OTHER INFORMATION: Amino acids 105-310 of Cts1 (Coccidioides
      posadiasii, GenBank AAA92643.1), with E145D, K205R, A214V, and
      G304M substitutions.

<400> SEQUENCE: 7

Val Tyr Gly Cys Ile Lys Gln Met Tyr Leu Leu Lys Lys Asn Asn Arg
1               5                   10                  15

Asn Leu Lys Thr Leu Leu Ser Ile Gly Gly Trp Thr Tyr Ser Pro Asn
            20                  25                  30

Phe Lys Thr Pro Ala Ser Thr Glu Asp Gly Arg Lys Lys Phe Ala Asp
        35                  40                  45

Thr Ser Leu Lys Leu Met Lys Asp Leu Gly Phe Asp Gly Ile Asp Ile
    50                  55                  60

Asp Trp Glu Tyr Pro Glu Asp Glu Lys Gln Ala Asn Asp Phe Val Leu
65                  70                  75                  80

Leu Leu Lys Ala Cys Arg Glu Ala Leu Asp Ala Tyr Ser Ala Lys His
                85                  90                  95

Pro Asn Gly Lys Arg Phe Leu Leu Thr Ile Ala Ser Pro Val Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Gly His Met Ser Asn Val Phe Pro Ser Thr Thr Lys Pro Glu Ser
145                 150                 155                 160

Thr Pro Phe Ser Ser Asp Lys Ala Val Lys Asp Tyr Ile Lys Ala Gly
                165                 170                 175

Val Pro Ala Asn Lys Ile Val Leu Gly Met Pro Leu Tyr Gly Arg Ala
            180                 185                 190

Phe Ala Ser Thr Asp Gly Ile Met Thr Ser Phe Asn Gly Val
```

195 200 205

<210> SEQ ID NO 8
<211> LENGTH: 206
<212> TYPE: PRT
<213> ORGANISM: Artificial Sequence
<220> FEATURE:
<223> OTHER INFORMATION: Amino acids 105-310 of Cts1 (Coccidioides posadiasii, GenBank AAA92643.1), with A151I, E191D, G203V, and G294L substitutions.

<400> SEQUENCE: 8

Val Tyr Gly Cys Ile Lys Gln Met Tyr Leu Leu Lys Lys Asn Asn Arg
1 5 10 15

Asn Leu Lys Thr Leu Leu Ser Ile Gly Gly Trp Thr Tyr Ser Pro Asn
20 25 30

Phe Lys Thr Pro Ala Ser Thr Glu Glu Gly Arg Lys Lys Phe Ile Asp
35 40 45

Thr Ser Leu Lys Leu Met Lys Asp Leu Gly Phe Asp Gly Ile Asp Ile
50 55 60

Asp Trp Glu Tyr Pro Glu Asp Glu Lys Gln Ala Asn Asp Phe Val Leu
65 70 75 80

Leu Leu Lys Ala Cys Arg Asp Ala Leu Asp Ala Tyr Ser Ala Lys His
85 90 95

Pro Asn Val Lys Lys Phe Leu Leu Thr Ile Ala Ser Pro Ala Gly Pro
100 105 110

Gln Asn Tyr Asn Lys Leu Lys Leu Ala Glu Met Asp Lys Tyr Leu Asp
115 120 125

Phe Trp Asn Leu Met Ala Tyr Asp Phe Ser Gly Ser Trp Asp Lys Val
130 135 140

Ser Gly His Met Ser Asn Val Phe Pro Ser Thr Thr Lys Pro Glu Ser
145 150 155 160

Thr Pro Phe Ser Ser Asp Lys Ala Val Lys Asp Tyr Ile Lys Ala Gly
165 170 175

Val Pro Ala Asn Lys Ile Val Leu Gly Met Pro Leu Tyr Leu Arg Ala
180 185 190

Phe Ala Ser Thr Asp Gly Ile Gly Thr Ser Phe Asn Gly Val
195 200 205

<210> SEQ ID NO 9
<211> LENGTH: 206
<212> TYPE: PRT
<213> ORGANISM: Artificial Sequence
<220> FEATURE:
<223> OTHER INFORMATION: Amino acids 105-310 of Cts1 (Coccidioides posadiasii, GenBank AAA92643.1), with K116H, G129V, G130L, A141I, E174D, K205R, K223R, D270E, R295H,and D301E substitutions.

<400> SEQUENCE: 9

Val Tyr Gly Cys Ile Lys Gln Met Tyr Leu Leu His Lys Asn Asn Arg
1 5 10 15

Asn Leu Lys Thr Leu Leu Ser Ile Val Leu Trp Thr Tyr Ser Pro Asn
20 25 30

Phe Lys Thr Pro Ile Ser Thr Glu Glu Gly Arg Lys Lys Phe Ala Asp
35 40 45

Thr Ser Leu Lys Leu Met Lys Asp Leu Gly Phe Asp Gly Ile Asp Ile
50 55 60

Asp Trp Glu Tyr Pro Asp Asp Glu Lys Gln Ala Asn Asp Phe Val Leu
65 70 75 80

-continued

```
Leu Leu Lys Ala Cys Arg Glu Ala Leu Asp Ala Tyr Ser Ala Lys His
                85                  90                  95

Pro Asn Gly Lys Arg Phe Leu Leu Thr Ile Ala Ser Pro Ala Gly Pro
            100                 105                 110

Gln Asn Tyr Asn Lys Leu Arg Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Gly His Met Ser Asn Val Phe Pro Ser Thr Thr Lys Pro Glu Ser
145                 150                 155                 160

Thr Pro Phe Ser Ser Glu Lys Ala Val Lys Asp Tyr Ile Lys Ala Gly
                165                 170                 175

Val Pro Ala Asn Lys Ile Val Leu Gly Met Pro Leu Tyr Gly His Ala
            180                 185                 190

Phe Ala Ser Thr Glu Gly Ile Gly Thr Ser Phe Asn Gly Val
        195                 200                 205


<210> SEQ ID NO 10
<211> LENGTH: 206
<212> TYPE: PRT
<213> ORGANISM: Artificial Sequence
<220> FEATURE:
<223> OTHER INFORMATION: Amino acids 105-310 of Cts1 (Coccidioides
      posadiasii, GenBank AAA92643.1), with Y106W, T139N, D175E, L184M,
      A198V, F206Y, N2554Q, P266I, K278R, and G289A substitutions.

<400> SEQUENCE: 10

Val Trp Gly Cys Ile Lys Gln Met Tyr Leu Leu Lys Lys Asn Asn Arg
1               5                   10                  15

Asn Leu Lys Thr Leu Leu Ser Ile Gly Gly Trp Thr Tyr Ser Pro Asn
            20                  25                  30

Phe Lys Asn Pro Ala Ser Thr Glu Glu Gly Arg Lys Lys Phe Ala Asp
        35                  40                  45

Thr Ser Leu Lys Leu Met Lys Asp Leu Gly Phe Asp Gly Ile Asp Ile
    50                  55                  60

Asp Trp Glu Tyr Pro Glu Glu Glu Lys Gln Ala Asn Asp Phe Val Met
65                  70                  75                  80

Leu Leu Lys Ala Cys Arg Glu Ala Leu Asp Ala Tyr Ser Val Lys His
                85                  90                  95

Pro Asn Gly Lys Lys Tyr Leu Leu Thr Ile Ala Ser Pro Ala Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Gly His Met Ser Gln Val Phe Pro Ser Thr Thr Lys Pro Glu Ser
145                 150                 155                 160

Thr Ile Phe Ser Ser Asp Lys Ala Val Lys Asp Tyr Ile Arg Ala Gly
                165                 170                 175

Val Pro Ala Asn Lys Ile Val Leu Ala Met Pro Leu Tyr Gly Arg Ala
            180                 185                 190

Phe Ala Ser Thr Asp Gly Ile Gly Thr Ser Phe Asn Gly Val
        195                 200                 205


<210> SEQ ID NO 11
<211> LENGTH: 206
```

-continued

<212> TYPE: PRT
<213> ORGANISM: Artificial Sequence
<220> FEATURE:
<223> OTHER INFORMATION: Amino acids 105-310 of Cts1 (Coccidioides posadiasii, GenBank AAA92643.1), with C108N, K116R, P140A, T143N, K156H, D164E, G165A, E174D, D175E, E176D, F182W, K187H, K205R, G250V, K261R, S268T, K285R, I286V, A296L, and S206Tsubstitutions.

<400> SEQUENCE: 11

```
Val Tyr Gly Asn Ile Lys Gln Met Tyr Leu Leu Arg Lys Asn Asn Arg
1               5                   10                  15

Asn Leu Lys Thr Leu Leu Ser Ile Gly Gly Trp Thr Tyr Ser Pro Asn
            20                  25                  30

Phe Lys Thr Ala Ala Ser Asn Glu Glu Gly Arg Lys Lys Phe Ala Asp
        35                  40                  45

Thr Ser Leu His Leu Met Lys Asp Leu Gly Phe Glu Ala Ile Asp Ile
    50                  55                  60

Asp Trp Glu Tyr Pro Asp Glu Asp Lys Gln Ala Asn Asp Trp Val Leu
65                  70                  75                  80

Leu Leu His Ala Cys Arg Glu Ala Leu Asp Ala Tyr Ser Ala Lys His
                85                  90                  95

Pro Asn Gly Lys Arg Phe Leu Leu Thr Ile Ala Ser Pro Ala Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ala Tyr Asp Phe Ser Gly Ser Trp Asp Lys Val
    130                 135                 140

Ser Val His Met Ser Asn Val Phe Pro Ser Thr Thr Arg Pro Glu Ser
145                 150                 155                 160

Thr Pro Phe Thr Ser Asp Lys Ala Val Lys Asp Tyr Ile Lys Ala Gly
                165                 170                 175

Val Pro Ala Asn Arg Val Val Leu Gly Met Pro Leu Tyr Gly Arg Leu
            180                 185                 190

Phe Ala Ser Thr Asp Gly Ile Gly Thr Thr Phe Asn Gly Val
        195                 200                 205
```

<210> SEQ ID NO 12
<211> LENGTH: 206
<212> TYPE: PRT
<213> ORGANISM: Artificial Sequence
<220> FEATURE:
<223> OTHER INFORMATION: Amino acids 105-310 of Cts1 (Coccidioides posadiasii, GenBank AAA92643.1), with K110R, K117H, L126V, K138R, E174D, D175E, L186V, R190K, A192V, K204H, K205R, A238I, S294T, K261R, S268T, D275E, A283L, G294A, G304I, and G309Msubstitutions.

<400> SEQUENCE: 12

```
Val Tyr Gly Cys Ile Arg Gln Met Tyr Leu Leu Lys His Asn Asn Arg
1               5                   10                  15

Asn Leu Lys Thr Leu Val Ser Ile Gly Gly Trp Thr Tyr Ser Pro Asn
            20                  25                  30

Phe Arg Thr Pro Ala Ser Thr Glu Glu Gly Arg Lys Lys Phe Ala Asp
        35                  40                  45

Thr Ser Leu Lys Leu Met Lys Asp Leu Gly Phe Asp Gly Ile Asp Ile
    50                  55                  60

Asp Trp Glu Tyr Pro Asp Glu Glu Lys Gln Ala Asn Asp Phe Val Leu
65                  70                  75                  80

Leu Val Lys Ala Cys Lys Glu Val Leu Asp Ala Tyr Ser Ala Lys His
                85                  90                  95
```

```
Pro Asn Gly His Arg Phe Leu Leu Thr Ile Ala Ser Pro Ala Gly Pro
            100                 105                 110

Gln Asn Tyr Asn Lys Leu Lys Leu Ala Glu Met Asp Lys Tyr Leu Asp
        115                 120                 125

Phe Trp Asn Leu Met Ile Tyr Asp Phe Ser Gly Ser Trp Asp Lys Val
    130                 135                 140

Thr Gly His Met Ser Asn Val Phe Pro Ser Thr Thr Arg Pro Glu Ser
145                 150                 155                 160

Thr Pro Phe Thr Ser Asp Lys Ala Val Lys Glu Tyr Ile Lys Ala Gly
                165                 170                 175

Val Pro Leu Asn Lys Ile Val Leu Gly Met Pro Leu Tyr Ala Arg Ala
            180                 185                 190

Phe Ala Ser Thr Asp Gly Ile Val Thr Ser Phe Asn Met Val
        195                 200                 205


<210> SEQ ID NO 13
<211> LENGTH: 49
<212> TYPE: DNA
<213> ORGANISM: Coccidioides immitis

<400> SEQUENCE: 13

ggatccccga attcatgagg ttccttattg gctttactta cttactctc                49


<210> SEQ ID NO 14
<211> LENGTH: 50
<212> TYPE: DNA
<213> ORGANISM: Coccidioides immitis

<400> SEQUENCE: 14

cgggatccat gatgatgatg atgatgactt ggcatcccat tcttcttgag               50


<210> SEQ ID NO 15
<211> LENGTH: 46
<212> TYPE: DNA
<213> ORGANISM: Coccidioides immitis

<400> SEQUENCE: 15

tacttccaat ccaatgcgat gtcaagtatg cccaattatt atccag                   46


<210> SEQ ID NO 16
<211> LENGTH: 51
<212> TYPE: DNA
<213> ORGANISM: Coccidioides immitis

<400> SEQUENCE: 16

tacttccaat ccaatgcgca aatgtacttg ctcaagaaga acaaccggaa c             51


<210> SEQ ID NO 17
<211> LENGTH: 51
<212> TYPE: DNA
<213> ORGANISM: Coccidioides immitis

<400> SEQUENCE: 17

ttatccactt ccaatgcgct aaacaccgtt gaagctagtg ccgatcccat c             51


<210> SEQ ID NO 18
<211> LENGTH: 57
<212> TYPE: DNA
<213> ORGANISM: Coccidioides immitis

<400> SEQUENCE: 18
```

-continued tacttccaat ccaatgcggt ttacggctgt atcaagcaaa tgtacttgct caagaag 57

<210> SEQ ID NO 19
<211> LENGTH: 58
<212> TYPE: DNA
<213> ORGANISM: Coccidioides immitis

<400> SEQUENCE: 19
ttatccactt ccaatgcgct aatcaaagcc aaggtccttc atcaacttca gagatgtg 58

<210> SEQ ID NO 20
<211> LENGTH: 53
<212> TYPE: DNA
<213> ORGANISM: Coccidioides immitis

<400> SEQUENCE: 20
tacttccaat ccaatgcgtc tctgaagttg atgaaggacc ttggctttga tgg 53

<210> SEQ ID NO 21
<211> LENGTH: 58
<212> TYPE: DNA
<213> ORGANISM: Coccidioides immitis

<400> SEQUENCE: 21
ttatccactt ccaatgcgct atgaagcaat agtgagcaag aatttcttgc cattcggg 58

<210> SEQ ID NO 22
<211> LENGTH: 55
<212> TYPE: DNA
<213> ORGANISM: Coccidioides immitis

<400> SEQUENCE: 22
tacttccaat ccaatgcgaa tggcaagaaa ttcttgctca ctattgcttc accgg 55

<210> SEQ ID NO 23
<211> LENGTH: 49
<212> TYPE: DNA
<213> ORGANISM: Coccidioides immitis

<400> SEQUENCE: 23
ttatccactt ccaatgcgct acatgtggcc agacactttg tcccagctg 49

<210> SEQ ID NO 24
<211> LENGTH: 45
<212> TYPE: DNA
<213> ORGANISM: Coccidioides immitis

<400> SEQUENCE: 24
tacttccaat ccaatgcgga cttcagcggc agctgggaca aagtg 45

<210> SEQ ID NO 25
<211> LENGTH: 51
<212> TYPE: DNA
<213> ORGANISM: Coccidioides immitis

<400> SEQUENCE: 25
ttatccactt ccaatgcgct aaacaccgtt gaagctagtg ccgatcccat c 51

<210> SEQ ID NO 26
<211> LENGTH: 7
<212> TYPE: PRT
<213> ORGANISM: Unknown
<220> FEATURE:

-continued

```
<223> OTHER INFORMATION: Linker

<400> SEQUENCE: 26

Gly Gly Gly Ala Ser Ala Ser
1               5


<210> SEQ ID NO 27
<211> LENGTH: 10
<212> TYPE: PRT
<213> ORGANISM: Unknown
<220> FEATURE:
<223> OTHER INFORMATION: Biotin Mimic

<400> SEQUENCE: 27

Ser Ala Trp Arg His Pro Gln Phe Gly Gly
1               5                   10
```

QUANTITATIVE ENZYME-LINKED IMMUNOASSAY (ELISA) TO APPROXIMATE COMPLEMENT FIXING ANTIBODY TITERS IN SERUM FROM PATIENTS WITH COCCIDIOIDOMYCOSIS

CROSS-REFERENCES TO RELATED APPLICATIONS

This application is a continuation-in-part and claims benefit of U.S. patent application Ser. No. 16/058,538 filed Aug. 8, 2018, which is a non-provisional and claims benefit of U.S. Patent Application 62/542,594 filed Aug. 8, 2017, the specification(s) of which is/are incorporated herein in their entirety by reference.

STATEMENT REGARDING FEDERALLY SPONSORED RESEARCH OR DEVELOPMENT

This invention was made with government support under Grant No. R01 AI132140 awarded by National Institutes of Health. The government has certain rights in the invention.

REFERENCE TO A SEQUENCE LISTING

Applicant asserts that the paper copy of the Sequence Listing is identical to the Sequence Listing in computer readable form found on the accompanying computer file, entitled UNIA_17_33_CIP_Sequence_Listing_ST25. The content of the sequence listing is incorporated herein by reference in its entirety.

FIELD OF THE INVENTION

The present invention features a recombinant Cts1 peptide and method to utilize the recombinant Cts1 peptide in an enzymes-linked immunoassay (ELISA) for the detection of a coccidioidomycosis infection.

BACKGROUND OF THE INVENTION

Coccidioidomycosis (CM), also known as San Joaquin Valley fever, is both a regionally and nationally important systemic fungal infection, often confused with other respiratory infections, cancer, or rheumatologic conditions. Because the clinical manifestations of CM overlap with such a diverse range of other illnesses, diagnosis typically requires specific laboratory testing. While direct microscopic detection of spherules in clinical specimens, growth of the fungus in culture, PCR detection of *Coccidioides*-specific of DNA sequence, or measurement of coccidioidal antigen are all clinically available approaches, diagnosis of CM is most frequently accomplished by detecting specific anti-coccidioidal antibodies in serum. Of the several serologic tests commercially performed for this purpose, the assay for anti-coccidioidal complement-fixing (CF) antibodies and the immunodiffusion method designed to measure the antibodies directed against the same antigen are the only tests whose quantitation has prognostic value, and for this reason they have remained in clinical use for over the past 60 years.

Despite its long history, the CF antibody assay has several limitations for all but the most specialized laboratories. Several biologics reagents (tanned sheep red blood cells, fresh serum complement, heat-sensitive coccidioidal antigen preparations) are required for the procedure, each of which can be obtained from diverse suppliers. The test is complex and labor-intensive. Day-to-day agreement among replicates is not always achieved and for this reason some laboratories repeat a prior specimen contemporaneously with a current one to determine more directly any difference in titer between the two. Recommended procedures are not uniform, there is no information available regarding differences obtained between different reference laboratories, and a national performance testing program has not been established. A method which avoided these limitations would be a useful alternative.

There is broad agreement that the protein within complex coccidioidal extracts that reacts with CF antibodies is the 427 amino acid product of the chitinase gene, CTS1, and its crystal structure has been determined. The recombinant expression product of CTS1 (rCTS1) has been considered as a reagent for an enzyme-linked immunoassay (ELISA) to measure CF antibodies, found to have potential, but was not pursued further. Truncations $rCTS1_{20-111}$ and $rCTS1_{280-427}$ were not reactive with sera from patients with CM. Little has been done further with these observations reported over twenty years ago, perhaps in large part because coccidioidomycosis is an orphan disease for which relatively small commercial incentive exists to improve its diagnosis and management.

Described herein, is additional work with recombinant products of truncations of rCTS1. The domain immunoreactive with antibodies is further restricted in serum from patients with CM and characterized the epitope(s) responsible for antibody binding. Also, assay results with reference to a standard curve, permitting expression of antibody binding as an antibody concentration instead of titers. These results support a recombinant truncation of CTS1 as a useful reagent for the eventual transition of quantitative CF antibody assays to an ELISA platform.

BRIEF SUMMARY OF THE INVENTION

It is an objective of the present invention to provide a recombinant Cts1 peptide composition and method to utilize the recombinant Cts1 peptide in an Enzyme-Linked Immunoassay (ELISA) that allow for the detection of a coccidioidomycosis infection, as specified in the independent claims. Embodiments of the invention are given in the dependent claims. Embodiments of the present invention can be freely combined with each other if they are not mutually exclusive.

The present invention features an isolated Cts1 peptide having sequence that is at least 90% identical to SEQ ID NO: 4 and containing at least one substitution modification relative to SEQ ID NO: 4.

Additionally, the present invention may feature an assay platform for detecting anti-coccidioidal antibodies. In some embodiments the platform comprises a solid support and an isolated Cts1 peptide having a sequence according to SEQ ID NO: 4 and containing at least one substitution modification relative to SEQ ID NO: 4, wherein the Cts1 is peptide attached to the solid support.

The present invention may also feature an isolated Cts1 peptide having a sequence that is at least 90% identical to SEQ ID NO: 4, wherein the Cts1 peptide is covalently attached to a component, wherein the component attaches to a peptide that is coated onto a solid support.

One of the unique and inventive technical features of the present invention is the use of a biotin-mimic tag sequence to orient the binding of the CTS1 peptide to a streptavidin coated well. Without wishing to limit the invention to any theory or mechanism, it is believed that the technical feature of the present invention advantageously provides for the CTS1 peptide conformation to be maintained and allows for an increase in sensitivity for the assay. This technical modification improves the quantitative ELISA assay. In general, ELISA assays are less complex, ELISA reagents are more readily available, the format is more familiar to clinical laboratories. Additionally, ELISAs are less labor intensive and can be automated. A quantitative ELISA measuring CS Abs to $rCTS1_{105-310}$ may be more sensitive than existing serologic tests for early coccidioidal infection. Additionally, methods and compositions of the present invention help reduce the non-specific antibody binding unrelated to acquiring a coccidioidal infection. This allows for a more sensitive test for early coccidioidal infection because signals could be distinguished at lower intensity, avoiding confusion with nonspecific antibody binding. None of the presently known prior references or work has the unique inventive technical feature of the present invention.

The present invention was able to determine a much smaller specific truncation of the 427 amino acid product of the chitinase gene, CTS1, that binds all of the highly specific anti-coccidioidal antibodies in serum than had been accomplished in the past. Previous truncations of the CTS1 protein showed binding to $rCTS1_{20-310}$, however, amino acids 20 to 309 were presently discovered to have no role in the binding. Additionally, truncations such as $rCTS1_{20-111}$ and $rCTS1_{280-427}$ were, also, shown to not be reactive with sera from patients with CM. The use of the CTS1 truncation (SEQ ID NO: 4) along with a single mutation helps to reduce the non-specific antibody binding unrelated to acquiring a coccidioidal infection. Overall, this provides a more sensitive test for early coccidioidal infection because signals could be distinguished at lower intensity, avoiding confusion with nonspecific antibody binding. Very surprisingly, smaller overlapping truncations from amino acid 110 to amino acid 310 showed virtually no specific antibody binding which unexpectedly indicates that all of the specific antibody binding is to sites dependent on conformation that is retained with SEQ ID NO: 4 but is not present on smaller portions of the truncation.

Furthermore, the prior references teach away from the present invention. For example, standard CF antibody assays are complex and labor intensive, with minimal reproducibility from day-to-day. Additionally, reagents are harder to obtain and may differ depending on the supplier in which it is acquired. Moreover, there are no uniform recommended procedures and no established national performance testing program. Furthermore, the inventive technical features of the present invention contributed to a surprising result. For example, the antibody binding to *Coccidioides*-specific epitope(s) depends upon conformation(s) present in the CTS1 peptide which is lost with the individual smaller peptides. Therefore, binding of serum antibodies to the CTS1 peptide was directed at conformational or discontinuous epitopes rather than epitopes of a primary amino acid sequence.

Additionally, although prior art has described an antigen enzyme immuno-assay (EIA) to detect coccidioidomycosis, prior assays were to detect individuals with more severe infections of coccidioidomycosis, described herein is a method to detect early infections. Furthermore, prior EIA assays use urine samples to detect galactomannans, however, the present invention uses serum samples to detect Cts1 protein. Therefore, one could not anticipate that because an EIA assay works with a protein detected in the urine that an EIA assay will be successful for detecting protein in a serum sample even if the two tests are to detect coccidioidomycosis infections.

Moreover, the present invention features an isolated Cts1 protein from the *Coccidioides posadasii* species. However, there are two *Coccidioides* species which can cause infection in humans, *C. posadasii* and *C. immitis*. The two species are morphologically identical, but their predicted proteins are only about 90% homologous. Therefore, to compare proteins between the species would potentially lead to minor differences in protein sequences. In the present invention, the SEQ ID NO: 4 is extracted from *C. posadasii* and has at least one mutation per that species protein.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A-1B show binding of anti-rCTS1(aa111-310) antibodies to rCTS1(aa111-310) after Ni-NTA affinity purification. FIG. 1A shows an SDS-PAGE rCTS1(aa20-310) (34.7 kDa) and rCTS1(aa111-310) (27.4 kDa). FIG. 1B shows an immunoblot of the same peptides with human CF+ sera. The larger bands are presumably dimers.

FIG. 2 shows an ELISA optical densities for IgG antibodies in human CF+ sera at different dilutions or PBS alone that bind to $rCTS1_{105-310}$, four overlapping peptides spanning $rCTS1_{105-310}$ (Frag1-Frag4), MBP alone, or PBS. The figure shows evidence of no binding for four subunits of Cts1, whereas $CTS_{105-310}$ has complete binding. This may be a prototype for a diagnostic test procedure.

Figure 5B:
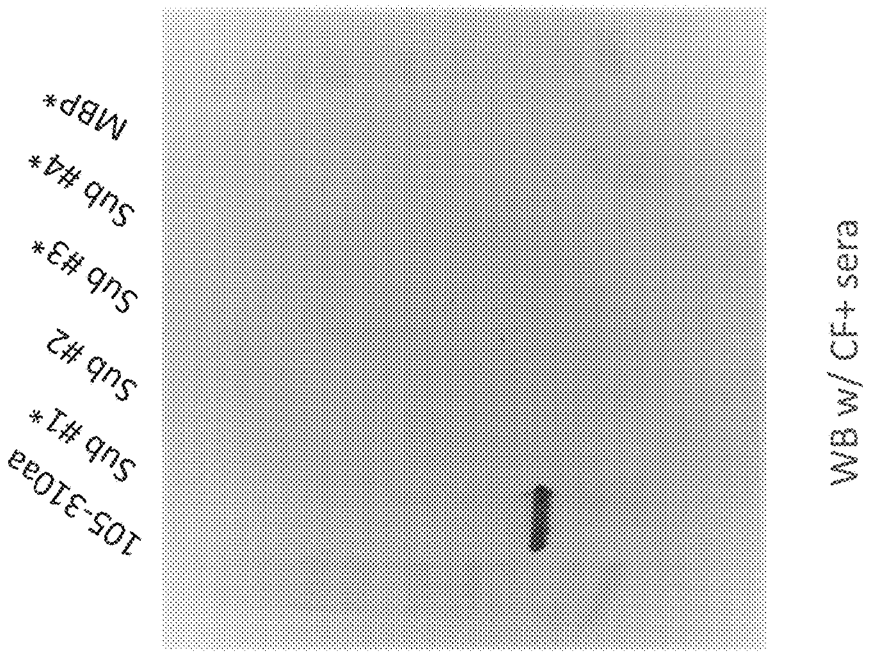
Figure 5A:
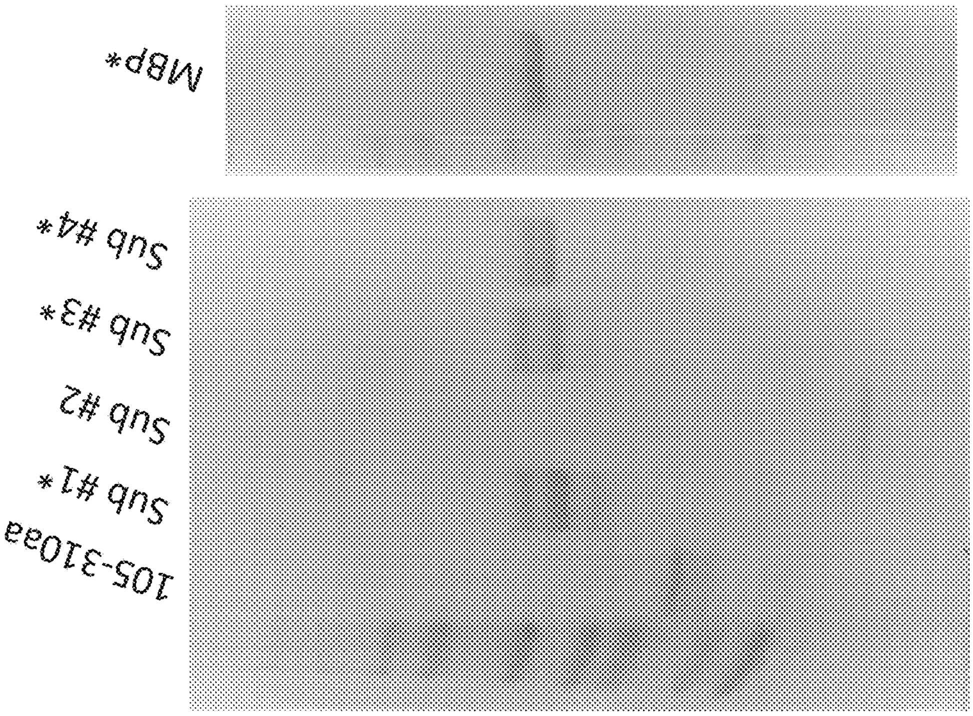

FIGS. 5A-5B show the lack of immunoreactivity of rCTS1 fragments 1-4. FIG. 5A shows an SDS PAGE and FIG. 5B shows an immunoblot of $rCTS1_{105-310}$, 4 subunits of $rCTS1_{105-310}$, and MBP probed with CF antibody-containing human sera. Only subunit #2 is cleaved from MBP.

Figure 6:
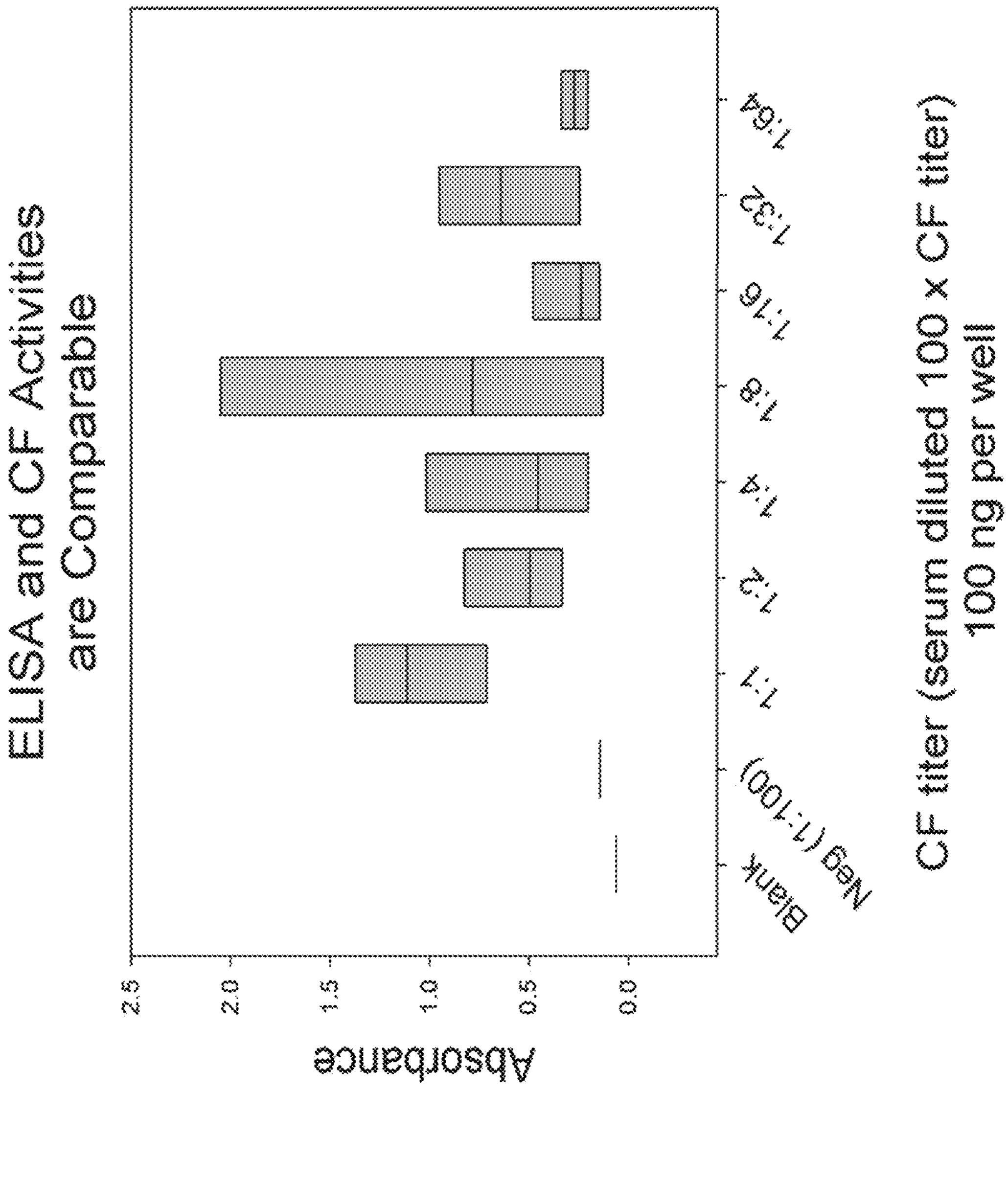

FIG. 6 shows ELISA and CF activities are comparable. Briefly, microtiter plates were prepared using 100 ng of CTS1 111-310 per well as described above. Human sera with CF titers from undetectable to 1:64 were diluted 1:100 and then proportionally to the CF titer. For example, sera of CF titer of 1:1 were diluted 1:100 and sera of CF titer of 1:64 were diluted 1:6400. Blocking prior to sera application, and enzyme conjugate detection of antibodies and absorbance measurements were conducted as described above.

DETAILED DESCRIPTION OF THE INVENTION

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

The present invention features methods and compositions for detecting coccidioidomycosis. Inventors surprisingly found that all or most of the antibody binding (CF antibody binding) is directed toward amino acids 105-310 or amino acids 111-310. The methods of the present invention allow for a specific detection above non-immune sera at a 1:100 dilution (an increase in sensitivity). The methods and compositions of the present invention will help reduce the non-specific antibody binding unrelated to acquiring a coccidioidal infection. This could provide a more sensitive test for early coccidioidal infection because signals could be distinguished at lower intensity, avoiding confusion with nonspecific antibody binding.

Terms

Unless otherwise explained, all technical and scientific terms used herein have the same meaning as commonly understood by one of ordinary skill in the art to which a disclosed invention belongs. The singular terms “a,” “an,” and “the” include plural referents unless context clearly indicates otherwise. Similarly, the word “or” is intended to include “and” unless the context clearly indicates otherwise. “Comprising” means “including.” Hence “comprising A or B” means “including A” or “including B” or “including A and B.”

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999, the disclosures of which are incorporated in their entirety herein by reference.

All publications, patent applications, patents, and other references mentioned herein are incorporated by reference in their entirety.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Sequence identity: The identity (or similarity) between two or more nucleic acid sequences is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Methods of alignment of sequences for comparison are well known in the art. Various programs and alignment algorithms are described in: Smith & Waterman, *Adv. Appl. Math,* 2:482, 1981; Needleman & Wunsch, *J. Mol. Biol.* 48:443, 1970; Pearson & Lipman, Proc. Natl. Acad. Sci. USA 85:2444, 1988; Higgins & Sharp, *Gene,* 73:237-44, 1988; Higgins & Sharp, CABIOS 5:151-3, 1989; Corpet et al, *Nuc. Acids Res,* 16:10881-90, 1988; Huang et al. *Computer Appls. in the Biosciences* 8, 155-65, 1992; and Pearson et al., *Meth. Mol. Bic.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J, Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN may be used to compare nucleic acid sequences, while BLASTP may be used to compare amino acid sequences. If the two compared sequences share homology, then the designated output file will present those regions of homology as aligned sequences. If the two compared sequences do not share homology, then the designated output file will not present aligned sequences. The BLAST-like alignment tool (BLAT) may also be used to compare nucleic acid sequences (Kent, *Genome Res.* 12:656-664, 2002). BLAT is available from several sources, including Kent Informatics (Santa Cruz, Calif.) and on the Internet (genome.ucsc.edu). Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth.

Sample: Any composition containing or presumed to contain a biomarker, or a composition being tested for the presence or absence of a particular biomarker or other biological entity such as an antibody or fragment thereof. Samples may include purified or separated components of cells, tissues, or blood, e.g., DNA, RNA, proteins, cell-free portions, or cell lysates. The sample can also be from a fresh liquid sample or a previously frozen sample. In certain embodiments, the sample is a liquid sample, e.g., blood or a blood component (plasma or serum), urine, semen, saliva, sputum, mucus, semen, tear, lymph, cerebral spinal fluid, material washed from a swab, etc. The sample can also be partially processed from a sample directly obtained from an individual.

Sensitivity: As used herein sensitivity may refer to the ability of a test to detect antibodies that are specifically produced by a patient's response to a coccidioidal infection. In some embodiments being more sensitive is to mean that a test is able to detect specific and therefore diagnostic antibodies than another test.

Referring now to FIGS. 1A-6, in some embodiments, the present invention features the use of a recombinant Cts1 peptide which is utilized in an ELISA assay for the detection of a coccidioidomycosis infection. For reference, the sequence for chitinase (SEQ ID NO: 1; *Coccidioides posadasii*, GenBank: AAA92643.1) is shown below in Table 1.

In other embodiments, the present invention features an isolated Cts1 peptide having a sequence that is at least 90% identical to SEQ ID NO: 4 and containing at least one substitution relative to SEQ ID NO: 4. Non-limiting embodiments of the isolated Cts1 peptides are shown in Table 1.

TABLE 1

Chitinase (Cts1) and isolated Cts1 peptide sequences

| SEQ ID NO: | DESCRIPTION | SEQUENCE |
|---|---|---|
| 1 | Chitinase (Cts1) | MRFLIGALLT LQTLVQASSM SSMPNYYPVP EAPAEGGFRS VVYFVNWAIY GRGHNPQDLK ADQFTHILYA FANIRPSGEV YLSDTWADTD KHYPGDKWDE PGNNVYGCIK QMYLLKKNNR NLKTLLSIGG WTYSPNFKTP ASTEEGRKKF ADTSLKLMKD LGFDGIDIDW EYPEDEKQAN DFVLLLKACR EALDAYSAKH PNGKKFLLTI ASPAGPQNYN KLKLAEMDKY LDFWNLMAYD FSGSWDKVSG HMSNVFPSTT KPESTPFSSD KAVKDYIKAG VPANKIVLGM PLYGRAFAST DGIGTSFNGV GGGSWENGVW DYKDMPQQGA QVTELEDIAA SYSYDKNKRY LISYDTVKIA GKKAEYITKN GMGGGMWWES SSDKTGNESL VGTVVNGLGG TGKLEQRENE LSYPESVYDN LKNGMPS |
| 2 | Cts1$_{20-310}$ | MSSMPNYYPVP EAPAEGGFRS VVYFVNWAIY GRGHNPQDLK ADQFTHILYA FANIRPSGEV YLSDTWADTD KHYPGDKWDE PGNNVYGCIK QMYLLKKNNR NLKTLLSIGG WTYSPNFKTP ASTEEGRKKF ADTSLKLMKD LGFDGIDIDW EYPEDEKQAN DFVLLLKACR EALDAYSAKH PNGKKFLLTI ASPAGPQNYN KLKLAEMDKY LDFWNLMAYD FSGSWDKVSG HMSNVFPSTT KPESTPFSSD KAVKDYIKAG VPANKIVLGM PLYGRAFAST DGIGTSFNGV |
| 3 | Cts1$_{111-310}$ | QMYLLKKNNR NLKTLLSIGG WTYSPNFKTP ASTEEGRKKF ADTSLKLMKD LGFDGIDIDW EYPEDEKQAN DFVLLLKACR EALDAYSAKH PNGKKFLLTI ASPAGPQNYN KLKLAEMDKY LDFWNLMAYD FSGSWDKVSG HMSNVFPSTT KPESTPFSSD KAVKDYIKAG VPANKIVLGM PLYGRAFAST DGIGTSFNGV |
| 4 | Cts1$_{105-310}$ | VYGCIK QMYLLKKNNR NLKTLLSIGG WTYSPNFKTP ASTEEGRKKF ADTSLKLMKD LGFDGIDIDW EYPEDEKQAN DFVLLLKACR EALDAYSAKH PNGKKFLLTI ASPAGPQNYN KLKLAEMDKY LDFWNLMAYD FSGSWDKVSG HMSNVFPSTT KPESTPFSSD KAVKDYIKAG VPANKIVLGM PLYGRAFAST DGIGTSFNGV |
| 5 | Modified Cts1$_{105-310}$ 99% identical to SEQ ID NO: 4; bold letters are substituted amino acids | VYGCIK QMYLLKKNNR NLKTLLSIGG WTYSPNFKTP ASTEEGRKKF ADTSLKLMKD LGFDGIDIDW EYPEDEKQAN DFVLLLKACR EA**V**DAYSAKH PNGKKFL**V**TI ASPAGPQNYN KLKLAEMDKY LDFWNLMAYD FSGSWDKVSG HMSNVFPSTT KPESTPFSSD KAVKDYIKAG VPANKIVLGM PLYGRAFAST DGIGTSFNGV |
| 6 | Modified Cts1$_{105-310}$ 99% identical to SEQ ID NO: 4: bold letters are substituted amino acids | VYGCIK QMYLLKKNNR NLKTLLSIGG WTYSPNFKTP ASTEEGRKKF **L**DTSLKLMKD LGFDGIDIDW EYP**D**DEKQAN DFVLLLKACR EALDAYSAKH PNGKKFLLTI ASPAGPQNYN KLKLAEMDKY LDFWNLMAYD FSGSWDKVSG HMSNVFPSTT KPESTPFSSD KAVKDYIKAG VPANKIVLGM PLYGRAFAST DGIGTSFNGV |

TABLE 1-continued

Chitinase (Cts1) and isolated Cts1 peptide sequences

| SEQ ID NO: | DESCRIPTION | SEQUENCE |
|---|---|---|
| 7 | Modified Cts1$_{105-310}$ 98% identical to SEQ ID NO: 4: bold letters are substituted amino acids | VYGCIK QMYLLKKNNR NLKTLLSIGG<br>WTYSPNFKTP ASTE**D**GRKKF ADTSLKLMKD<br>LGFDGIDIDW EYPEDEKQAN DFVLLLKACR<br>EALDAYSAKH PNGK**R**FLLTI ASP**V**GPQNYN<br>KLKLAEMDKY LDFWNLMAYD FSGSWDKVSG<br>HMSNVFPSTT KPESTPFSSD KAVKDYIKAG<br>VPANKIVLGM PLYGRAFAST DGI**M**TSFNGV |
| 8 | Modified Cts1$_{105-310}$ 98% identical to SEQ ID NO: 4; bold letters are substituted amino acids | VYGCIK QMYLLKKNNR NLKTLLSIGG<br>WTYSPNFKTP ASTEEGRKKF **I**DTSLKLMKD<br>LGFDGIDIDW EYPEDEKQAN DFVLLLKACR<br>**D**ALDAYSAKH PN**V**KKFLLTI ASPAGPQNYN<br>KLKLAEMDKY LDFWNLMAYD FSGSWDKVSG<br>HMSNVFPSTT KPESTPFSSD KAVKDYIKAG<br>VPANKIVLGM PLY**L**RAFAST DGIGTSFNGV |
| 9 | Modified Cts1$_{105-310}$ 95% identical to SEQ ID NO: 4; bold letters are substituted amino acids | VYGCIK QMYLL**H**KNNR NLKTLLSI**VL**<br>WTYSPNFKTP **I**STEEGRKKF ADTSLKLMKD<br>LGFDGIDIDW EYP**D**DEKQAN DFVLLLKACR<br>EALDAYSAKH PNGK**R**FLLTI ASPAGPQNYN<br>KL**R**LAEMDKY LDFWNLMAYD FSGSWDKVSG<br>HMSNVFPSTT KPESTPFSS**E** KAVKDYIKAG<br>VPANKIVLGM PLYG**H**AFAST **E**GIGTSFNGV |
| 10 | Modified Cts1$_{105-310}$ 95% identical to SEQ ID NO: 4; bold letters are substituted amino acids | V**W**GCIK QMYLLKKNNR NLKTLLSIGG<br>WTYSPNFK**N**P ASTEEGRKKF ADTSLKLMKD<br>LGFDGIDIDW EYPE**E**EKQAN DFV**M**LLKACR<br>EALDAYSVKH PNGKK**Y**LLTI ASPAGPQNYN<br>KLKLAEMDKY LDFWNLMAYD FSGSWDKVSG<br>HMS**Q**VFPSTT KPEST**I**FSSD KAVKDYI**R**AG<br>VPANKIVL**A**M PLYGRAFAST DGIGTSFNGV |
| 11 | Modified Cts1$_{105-310}$ 90% identical to SEQ ID NO: 4: bold letters are substituted amino acids | VYG**N**IK QMYLL**R**KNNR NLKTLLSIGG<br>WTYSPNFKT**A** AS**N**EEGRKKF ADTSL**H**LMKD<br>LGF**EA**IDIDW EYP**DED**KQAN D**W**VLLL**H**ACR<br>EALDAYSAKH PNGK**R**FLLTI ASPAGPQNYN<br>KLKLAEMDKY LDFWNLMAYD FSGSWDKVS**V**<br>HMSNVFPSTT **R**PESTPF**T**SD KAVKDYIKAG<br>VPAN**RV**VLGM PLYGR**L**FAST DGIGT**T**FNGV |
| 12 | Modified Cts1$_{105-310}$ 90% identical to SEQ ID NO: 4; bold letters are substituted amino acids | VYGCI**R** QMYLLK**H**NNR NLKTL**V**SIGG<br>WTYSPNF**R**TP ASTEEGRKKF ADTSLKLMKD<br>LGFDGIDIDW EYP**DE**EKQAN DFVLL**V**KAC**K**<br>E**V**LDAYSAKH PNG**HR**FLLTI ASPAGPQNYN<br>KLKLAEMDKY LDFWNLM**I**YD FSGSWDKV**T**G<br>HMSNVFPSTT **R**PESTPF**T**SD KAVK**E**YIKAG<br>VP**L**NKIVLGM PLY**A**RAFAST DGI**V**TSFN**M**V |

In some embodiments, the Cts1 peptide has a sequence that is 100% identical to SEQ ID NO: 4. In some embodiments, the Cts1 peptide has a sequence that is 99% identical to SEQ ID NO: 4. In some embodiments, the Cts1 peptide has a sequence that is 98% identical to SEQ ID NO: 4. In some embodiments, the Cts1 peptide has a sequence that is 97% identical to SEQ ID NO: 4. In some embodiments, the Cts1 peptide has a sequence that is 96% identical to SEQ ID NO: 4. In some embodiments, the Cts1 peptide has a sequence that is 95% identical to SEQ ID NO: 4. In some embodiments, the Cts1 peptide has a sequence that is 90% identical to SEQ ID NO: 4. In some embodiments, the Cts1 peptide has a sequence that is 85% identical to SEQ ID NO: 4. In some embodiments, the Cts1 peptide has a sequence that is 80% identical to SEQ ID NO: 4. In some embodiments, the Cts1 peptide has a sequence that is 75% identical to SEQ ID NO: 4. In some embodiments, the Cts1 peptide has a sequence that is 70% identical to SEQ ID NO: 4. Non-limiting examples of peptides that are similar to SEQ ID NO: 4 are shown in Table 1.

In other embodiments, the present invention also features peptides that are similar to SEQ ID NO: 4, e.g., peptides wherein one amino acid is different, two amino acids are different, three amino acids are different, four amino acids are different, five amino acids are different, six amino acids are different, seven amino acids are different, eight amino acids are different, nine amino acids are different, ten amino acids are different, more than 10 amino acids are different, more than 20 amino acids are different, more than 30 amino acids are different, 20-30 amino acids are different, 1-10 amino acids are different, 10-20 amino acids are different, 30-40 amino acids are different, 40-50 amino acids are different, etc. Non-limiting examples of peptides that are similar to SEQ ID NO: 4 are shown in Table 1.

In some embodiments, the present invention provides an isolated peptide according to SEQ ID NO: 3. The present invention also feature peptides that are similar to SEQ ID NO: 3, e.g., peptides wherein one amino acid is different, two amino acids are different, three amino acids are different, four amino acids are different, five amino acids are different, six amino acids are different, seven amino acids are different, eight amino acids are different, nine amino acids are different, ten amino acids are different, more than 10 amino acids are different, more than 20 amino acids are different, more than 30 amino acids are different, 20-30 amino acids are different, 1-10 amino acids are different, 10-20 amino acids are different, 30-40 amino acids are different, 40-50 amino acids are different, etc. Stated differently, in some embodiments, the peptide is at least 75% identical to SEQ ID NO: 3. In some embodiments, the peptide is at least 80% identical to SEQ ID NO: 3. In some embodiments, the peptide is at least 85% identical to SEQ ID NO: 3. In some embodiments, the peptide is at least 90% identical to SEQ ID NO: 3. In some embodiments, the peptide is at least 95% identical to SEQ ID NO: 3. In some embodiments, the peptide is at least 96% identical to SEQ ID NO: 3. In some embodiments, the peptide is at least 97% identical to SEQ ID NO: 3. In some embodiments, the peptide is at least 98% identical to SEQ ID NO: 3. In some embodiments, the peptide is at least 99% identical to SEQ ID NO: 3. In some embodiments, the peptide is at least 100% identical to SEQ ID NO: 3.

In some embodiments, the isolated Cts1 peptide has a sequence according to SEQ ID NO: 5. In some embodiments, the isolated Cts1 peptide has a sequence according to SEQ ID NO: 6. In some embodiments, the isolated Cts1 peptide has a sequence according to SEQ ID NO: 7. In some embodiments, the isolated Cts1 peptide has a sequence according to SEQ ID NO: 8. In some embodiments, the isolated Cts1 peptide has a sequence according to SEQ ID NO: 9. In some embodiments, the isolated Cts1 peptide has a sequence according to SEQ ID NO: 10. In some embodiments, the isolated Cts1 peptide has a sequence according to SEQ ID NO: 11. In some embodiments, the isolated Cts1 peptide has a sequence according to SEQ ID NO: 12.

In some embodiments, the Cts1 peptide having a sequence of the above-mentioned mentioned sequences has a sequence that is at least 100% identical to the aforementioned sequences. In some embodiments, the Cts1 peptide having a sequence of the above-mentioned sequences has a sequence that is at least 99% identical to the aforementioned sequences. In some embodiments, the Cts1 peptide having a sequence of the above-mentioned sequences has a sequence that is at least 98% identical to the aforementioned sequences. In some embodiments, the Cts1 peptide having a sequence of the above-mentioned sequences has a sequence that is at least 97% identical to the aforementioned sequences. In some embodiments, the Cts1 peptide having a sequence of the above-mentioned sequences has a sequence that is at least 96% identical to the aforementioned sequences. In some embodiments, the Cts1 peptide having a sequence of the above-mentioned sequences has a sequence that is at least 95% identical to the aforementioned sequences. In some embodiments, the Cts1 peptide having a sequence of the above-mentioned sequences has a sequence that is at least 90% identical to the aforementioned sequences. In some embodiments, the Cts1 peptide having a sequence of the above-mentioned sequences has a sequence that is at least 85% identical to the aforementioned sequences. In some embodiments, the Cts1 peptide having a sequence of the above-mentioned sequences has a sequence that is at least 80% identical to the aforementioned sequences. In some embodiments, the Cts1 peptide of having a sequence of the above-mentioned sequences has a sequence that is at least 75% identical to the aforementioned sequences.

The present invention may also feature peptides that are similar to the aforementioned sequences, e.g., peptides wherein one amino acid is different, two amino acids are different, three amino acids are different, four amino acids are different, five amino acids are different, six amino acids are different, seven amino acids are different, eight amino acids are different, nine amino acids are different, ten amino acids are different, more than 10 amino acids are different, more than 20 amino acids are different, more than 30 amino acids are different, 20-30 amino acids are different, 1-10 amino acids are different, 10-20 amino acids are different, 30-40 amino acids are different, 40-50 amino acids are different, etc.

The present invention also features nucleic acids that encode any of the peptides disclosed herein (e.g., nucleic acids that encode SEQ ID NO: 3, SEQ ID NO: 4, a peptide similar thereto, etc.).

The present invention also provides expression vectors that can produce any of the peptides disclosed herein.

The present invention also provides peptide constructs comprising one of the peptides disclosed herein (e.g., SEQ ID NO: 4, SEQ ID NO: 3, etc.) attached to or linked (directly or indirectly) to a component used to bind the peptide to a solid support. Methods and reagents used for linking or binding a peptide to a solid support are well known to one of ordinary skill in the art.

In some embodiments, the Cts1 peptide is attached to a solid support. In some embodiments, the Cts1 peptide is covalently bound to a solid support. In other embodiments, the Cts1 peptide is non-covalently bound to a solid support. In some embodiments, a solid support may include but is not limited to solid surface, plastic, or streptavidin-coated plate.

In some embodiments, the Cts1 peptide is covalently attached to a component. In some embodiments, the Cts1 peptide is covalently bound to a component. In some embodiments, the Cts1 peptide is non-covalently attached to a component. In some embodiments, the Cts1 peptide is non-covalently bound to a component. In some embodiments, the component attaches the Cts1 peptide to a peptide that is on a solid support. Non-limiting examples of the component may include but are not limited to biotin, a biotin mimic (SEQ ID NO: 27), a linker (SEQ ID NO: 26) or a peptide sequence that comprises SEQ ID NO: 26 followed by SEQ ID NO: 27. In other embodiments, a component may include additional amino acid sequences that bind to streptavidin like biotin does.

In some embodiments, the isolated Cts1 peptide is covalently attached to a component, wherein the component attaches to a peptide that is on a solid support.

In some embodiments, the isolated Cts1 peptide maintains its conformational shape. In other embodiments, the isolated Cts1 peptide maintains its conformational shape while attached to a component. In other embodiments, the isolated Cts1 peptide maintains its conformational shape while covalently attached to a component. In other embodiments, the isolated Cts1 peptide maintains its conformational shape while non-covalently attached to a component. In some embodiments, the isolated Cts1 peptide maintains its conformational shape while bound to a component. In other embodiments, the isolated Cts1 peptide maintains its conformational shape while covalently bound to a component. In other embodiments, the isolated Cts1 peptide maintains its conformational shape while non-covalently bound to a component.

The present invention may feature an assay platform for detecting anti-coccidioidal antibodies. In some embodiments, the platform comprises a solid support. In other embodiments the platform comprises an isolated Cts1 peptide having a sequence according to SEQ ID NO: 4 and containing at least one substitution modification relative to SEQ ID NO: 4, wherein the Cts1 peptide is attached to the solid support.

In some embodiments, the isolated Cts1 peptide has a sequence according to SEQ ID NO: 5. In some embodiments, the isolated Cts1 peptide has a sequence according to SEQ ID NO: 6. In some embodiments, the isolated Cts1 peptide has a sequence according to SEQ ID NO: 7. In some embodiments, the isolated Cts1 peptide has a sequence according to SEQ ID NO: 8. In some embodiments, the isolated Cts1 peptide has a sequence according to SEQ ID NO: 9. In some embodiments, the isolated Cts1 peptide has a sequence according to SEQ ID NO: 10. In some embodiments, the isolated Cts1 peptide has a sequence according to SEQ ID NO: 11. In some embodiments, the isolated Cts1 peptide has a sequence according to SEQ ID NO: 12.

Without wishing to limit the invention to any theory or mechanism, it is believed that the substitution modification helps improve sensitivity and/or helps eliminate cross reactivity.

In some embodiments, the assay platform is for an ELISA assay. In some embodiments, the platform is for a complement fixation assay.

In some embodiments, the solid support is a well. In some embodiments, the well is a part of a microwell plate. In some embodiments, the solid support is a microwell. In other embodiments, the solid support is a microwell plate. In other embodiments, the solid support is a solid surface. In some embodiments, the solid support is plastic. In some embodiments, the solid support is a streptavidin-coated plate.

In some embodiments, the isolated Cts1 peptide is covalently attached to a component. In some embodiments, the component attaches to a peptide that is on a solid support. In some embodiments, the isolated Cts1 peptide maintains its conformational shape. In other embodiments, the isolated Cts1 peptide maintains its conformational shape while attached to the platform. In some embodiments, the isolated Cts1 peptide maintains its conformational shape while attached to a solid support. Non-limiting examples of the component may include but are not limited to biotin, a biotin mimic (SEQ ID NO: 27), a linker (SEQ ID NO: 26) or a peptide sequence that comprises SEQ ID NO: 26 followed by SEQ ID NO: 27.

Additionally, the present invention may feature an isolated Cts1 peptide having a sequence that is at least 90% identical to SEQ ID NO: 4, wherein the Cts1 peptide is covalently attached to a component, wherein the component attaches to a peptide that is coated onto a solid support. In some embodiments, the isolated Cts1 peptide maintains its conformational shape.

The present invention also provides assay platforms for detecting anti-coccidioidal antibodies. For example, the assay platform may comprise a surface, such as a well, wherein a peptide of the present invention (e.g., SEQ ID NO: 4) is bound to the surface. A sample may be introduced to the assay platform, wherein the sample is contacted with the peptide bound to the surface. Assays such as this may be similar to an ELISA.

In some embodiments, the surface the peptide is bound to may include but is not limited to a solid support, a solid surface, plastic, or streptavidin-coated plate. In other embodiments, the peptide may be attached to the surface by, but not limited to, biotin, a biotin mimic (SEQ ID NO: 27), a linker (SEQ ID NO: 26) or a peptide sequence that comprises SEQ ID NO: 26 followed by SEQ ID NO: 27. In other embodiments, the peptide may be attached to the surface by other amino acid sequences that bind to streptavidin like biotin does.

EXAMPLE

The following is a non-limiting example of the present invention. It is to be understood that said example is not intended to limit the present invention in any way. Equivalents or substitutes are within the scope of the present invention.

Methods:

Human sera. A serum library composed of remnant specimens tested for anti-coccidioidal antibodies by immunodiffusion at the Southern Arizona Veterans Health Care System Medical Center was used for these studies. All specimens were de-identified, and the University of Arizona Institutional Review Board has determined that their use was not human experimentation. For some studies, a serum pool was created from portions of 50 separate sera. The calculated geometric mean CF titer for the sum of the individual sera was 1:12, and when the pool was tested directly by quantitative immunodiffusion, the titer was 1.8.

Recombinant antigen preparation. Full-length (FL) CTS1 was produced by FOR from a cDNA library (Dugger K O, Villareal K M, Nguyen A, Zimmermann C R, Law J H, Galgiani J N. Cloning and sequence analysis of the cDNA for a protein from *Coccidioides posadasii* with immunogenic potential. BiochemBiophysResCommun 1996; 218 (2): 485-9) using primers shown in Table 2. Sequence for this amplimer matched that submitted to Genbank (U60807) (Zimmermann C R, Johnson S M, Martens G W, White A G, Pappagianis D. Cloning and expression of the complement fixation antigen-chitinase of *Coccidioides immitis*. Infect Immun 1996; 64(12): 4967-75). Truncations of and modifications of rCTS1 were prepared by PCR using primers also shown in Table 2.

TABLE 2

Primers used to produce rCTS1 and its truncations.

| # | Name | Amino Acid | DNA Sequence | SEQ ID NO.: |
|---|---|---|---|---|
| FL | CF-1 | 1-*** | GGATCCCCGAATTCATGAGGTTCCTT ATTGGCTTTACTTACTTACTCTC | 13 |
| FL | CF-427 | ***-427 | CGGGATCCATGATGATGATGATGATG ACTTGGCATCCCATTCTTCTTGAG | 14 |
| 1 | 20-Fw | 20-*** | TACTTCCAATCCAATGCGATGTCAAG TATGCCCAATTATTATCCAG | 15 |
| 2a | 111-Fw | 111-** | TACTTCCAATCCAATGCGCAAATGTA CTTGCTCAAGAAGAACAACCGGAAC | 16 |
| 3 | 310-Rv | ***-310 | TTATCCACTTCCAATGCGCTAAACAC CGTTGAAGCTAGTGCCGATCCCATC | 17 |
| 3a | 310_BMP_Rv | ***-310 | TTATCCACTTCCAATGCGCTACCACC GAACTGCGGGTGACGCCAAGCGGAG CTGGCGCTGGCGCCGCCGCCAACAC CGTTGAAGCTAGT | 18 |
| 2b | Frag1_105_Fw | 105-*** | TACTTCCAATCCAATGCGGTTTACGG CTGTATCAAGCAAATGTACTTGCTCA AGAAG | 19 |

TABLE 2-continued

Primers used to produce rCTS1 and its truncations.

| # | Name | Amino Acid | DNA Sequence | SEQ ID NO.: |
|---|---|---|---|---|
| 4 | Frag1_ 164_Rv | ***-164 | TTATCCACTTCCAATGCGCTAATCAAA GCCAAGGTCCTTCATCAACTTCAGAG ATGTG | 20 |
| 5 | Frag2_ 154_Fw | 154--** | TACTTCCAATCCAATGCGTCTCTGAA GTTGATGAAGGACCTTGGCTTTGATG G | 21 |
| 6 | Frag2_ 212_Rv | ***-212 | TTATCCACTTCCAATGCGCTATGAAG CAATAGTGAGCAAGAATTTCTTGCCA TTCGGG | 22 |
| 7 | Frag3_ 202_Fw | 202-*** | TACTTCCAATCCAATGCGAATGGCAA GAAATTCTTGCTCACTATTGCTTCACC GG | 23 |
| 8 | Frag3_ 252_Rv | ***-252 | TTATCCACTTCCAATGCGCTACATGT GGCCAGACACTTTGTCCCAGCTG | 24 |
| 9 | Frag4_ 240_Fw | 240-*** | TACTTCCAATCCAATGCGGACTTCAG CGGCAGCTGGGACAAAGTG | 25 |

Figure 1B:
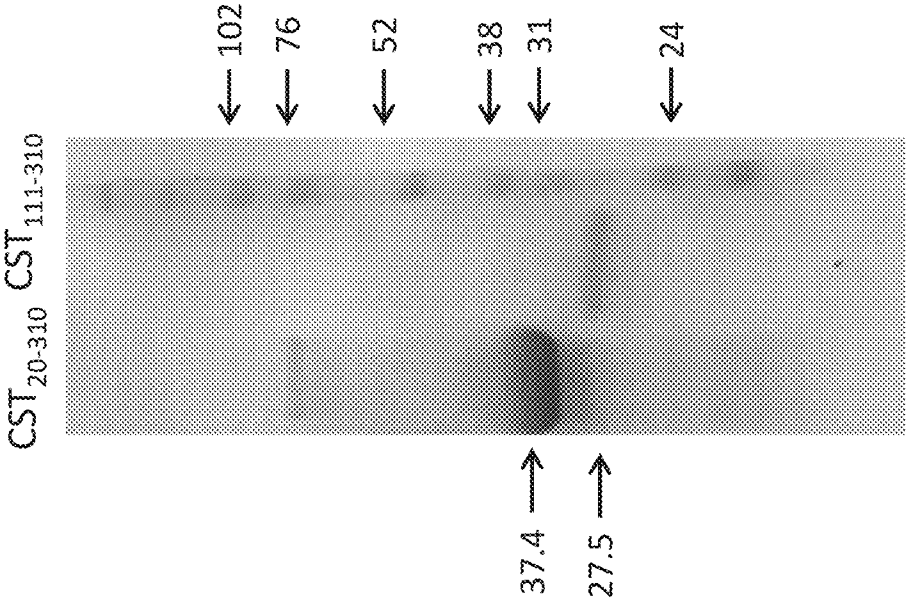
Figure 1A:
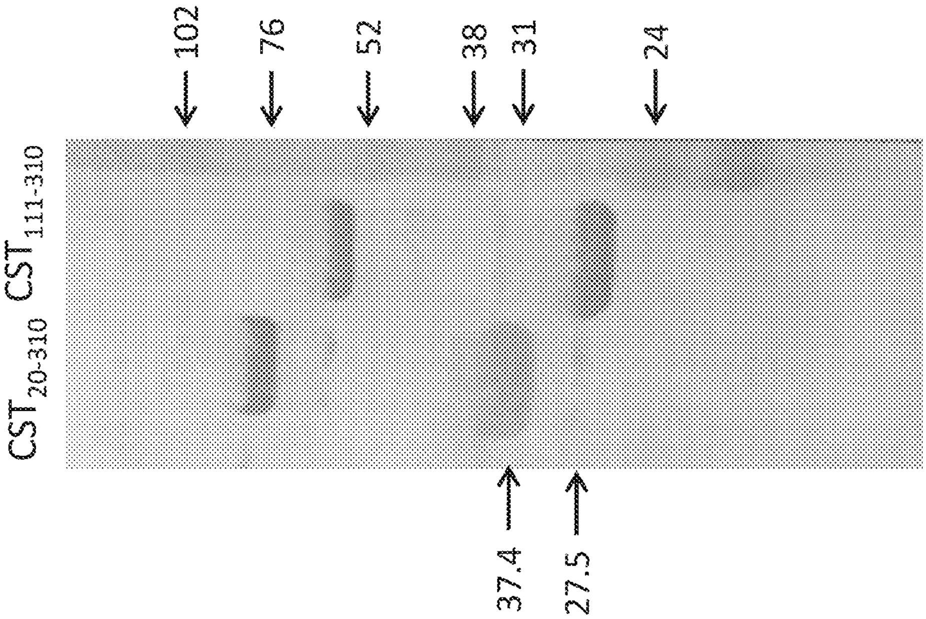

For initial studies with rCTS1$_{20-310}$ (SEQ ID NO: 2) and rCTS1$_{111-310}$ (SEQ ID NO: 3) were expressed in *Escherichia coil* BL21 DE3 gold and extracted with 8M urea buffers and disrupted by ultrasound treatment at room temperature for 1 hour. The purification was accomplished by affinity binding to nickel-NTA column. After collecting and pooling eluate fractions containing the expressed peptide as judged by SDS-PAGE and immunoblot, the pool was placed in dialysis tubing, and the urea was slowly removed by making twice daily 1-liter changes of the renaturation buffer (150 mM of Sodium Chloride (NaCl), 1 mM of Ethylenediaminetetraacetic acid (EDTA), 5 mM of Glutathione reduced (GSH), 0.5 mM of Glutathione oxidized (GSSG), 20 mM of Tris pH9.5 and 10% of Glycerol). The stepwise gradient of urea was 6.5, 5, 3.5, 1, and 0 M. Following renaturation (e.g., dialyze to PBS), gel-filtration was conducted with a P100 fine (Bio-Rad) 50 ml packed in an adaptor column 2.0+20 cm at a flow rate of 0.1 ml/min, Proteins were analyzed by PAGE and subsequent immunoblotting, for example, FIG. 1B shows SDS PAGE of *E. coli*-expressed rCTS1 truncations after Ni-NTA affinity purification. FIG. 1A shows an immunoblot of *E. coli*-expressed rCTS1 truncations with CF+ human serum.

For subsequent studies, amplimers were cloned into Ligation Independent

Cloning Vectors pMCSG7 that contained a T7 promoter and N-terminal His-tag, as described Eschenfeldt et al 2009 (Eschenfeldt W H, Lucy 5, Millard C S, Joachimiak A, Mark I D. A family of LIC vectors for high-throughput cloning and purification of proteins. Methods Mol Biol 2009; 498; 105-15) and confirmed by sequencing. The rCTS1$_{105-310}$ truncation was soluble upon *E. coli* lysis, and thus, did not need to be refolded as a step of collection. Further, it gave significantly higher yield per gram of bacterial pellet than the rCTS1$_{105-310}$ truncation. Thus, the rCTS1$_{105-310}$ truncation was used in place of the rCTS1$_{111-310}$ truncation. An additional construct of rCTS1$_{105-310}$ involved creating a biotin mimetic protein tag at the C-terminal end of the aa105-310 truncation by adding a linker region GGGASAS (SEQ ID NO: 26) followed by the decapeptide, SAWRHPQFGG (SEQ ID NO: 27) via PCR.

Vectors for the various rCTS1 constructs were cloned into *Escherichia coli* BL21 DE3 gold cells and purified as in Neubert et al. 2017 (Neubert M J, Dahlmann E A, Ambrose A, Johnson M D L. Copper Chaperone CupA and Zinc Control CopY Regulation of the Pneumococcal cop Operon. mSphere 2017; 2(5)) with modifications. After initial purification using immobilized nickel-affinity chromatography (IMAC) (HisTrap FF, GE Healthcare), protein was further purified by size-exclusion chromatography (SEC) (Superdex 200, GE Healthcare) using a buffer of 20 mM Tris pH 8, 200 mM NaCl, and 5% glycerol. Additionally, using the primers shown in Table 2, four fragments were made of the aa105-310 truncation: Fragment 1 (aa105-164), Fragment 2 (aa154-212), Fragment 3 (aa202-252), and Fragment 4 (aa240-310). Based on either no peak or observable band on a gel from the nickel elution, fragments #1, 3, and 4 were determined to be insoluble. To resolve this, truncations for these fragments were cloned into pMCSG9 that contained a maltose binding protein (MBP) linker to increase solubility, and the growth and purification process repeated. SEC peaks containing pure rCTS1 truncation fragments (as determined by SDS-PAGE), with (fragments #1, 3, 4) or without (fragment #2) MBP were concentrated if necessary (i.e. Amicon® Ultra Centrifugal Filters with molecular weight cut-offs) and concentration was determined by absorbance at 280 nm using molecular weight and extinction coefficient. Samples at >10 μM were aliquoted into thin-walled FOR tubes, and flash-frozen using liquid $N_2$ Immunoblot analysis. All expression products were analyzed on standard SDS PAGE. Because truncations differed in size, peptides were calculated in molarity and approximately 200 um/lane of each soluble peptide was loaded equally on 4-20% Ready GEL (Bio-Rad, Cat #4561093), and subsequently the gels were stained with Coomassie. Separated proteins were transferred from the gel to a nitrocellulose membrane, rinsed with Tris-buffered saline containing 0.05% Tween-20 (TBST) before blocking with 5% normal goat sera (NGS) in TBS-T for either one hour at room temperature or overnight at 4° C. Two identical immunoblots were performed, one with sera from the serum bank (CF=1:128) and the other with normal human serum. The sera were diluted 1:1000. Immunoblots were then washed, stained with alkaline phosphatase-conjugated goat anti-human IgG antibody, washed again, and immunoreactive bands visualized with colorimetric alkaline phosphatase substrate reagents.

As indicated in the results, for one competition study, a truncation (rCTS1$_{111-310}$) was mixed with the CF+ sera at 1 mM or 10 mM (5× or 50× the amount that was loaded to the gel) prior to application to the membrane and resulting binding to rCTS1(aa20-310) was assessed.

Immunoblots demonstrated that both the a.a. 20-310 (Cts1$_{20-310}$; SEQ ID NO: 2) and the a.a. 111-310 (Cts1$_{111-310}$; SEQ ID NO: 3) recombinant peptides reacted to sera from patients with coccidioidomycosis that contained CF antibodies but did not react with sera from uninfected patients. Absorption of CF positive sera with a.a. 111-310 (Cts1$_{111-310}$; SEQ ID NO: 3) eliminated immunoblot binding of the sera to a.a. 20-310 (Cts1$_{20-310}$; SEQ ID NO; 2) (data not shown).

ELISA. Initial studies were carried out by coating standard plastic 96-well microplates (Thermo Scientific, Cat, #80040E0910) with 100 ng/well of recombinant peptides at 4° C. for overnight. Preliminary studies demonstrated that his amount of peptide per well was not rate-limiting. After triplicate washing with PBST, coated wells were blocked with 5% milk in PBST at room temperature for 30 min, excess was removed, and 100 μl of the serum pool, or individual human CF+ sera used to prepare the pool were added to duplicate wells at various dilutions. Duplicate wells filled with PBS were also included. After incubation at room temperature for 1 hour, wells were washed 3 times with PBST. Then, affinity-purified peroxidase-labeled goat anti-human IgG antibodies (KPL, Cat. #474-1006, diluted 1:10,000) was added and left at room temperature for 1 h, after which the wells were washed 3 times with PBST. Finally, SuperBlue TMB Microwell Peroxidase Substrate (KPL Cat. #52-00-02) was added and 10 min later 1N HCl stop solution is added. Optical densities (OD) were read at 450 nm, Same-day standard ELISA curves were produced by coating wells with goat anti-human antibody (IgG) or PBS and incubated with human immunoglobulin at concentrations from 2-14 ng/ml. Experimental OD measurements minus background were plotted on the standard curves within the OD range of 0.10 to 0.80, multiplied by the serum dilution factor and expressed as μg/ml of IgG.

For later studies, Pierce Streptavidin coated high binding capacity 96-well plates (Thermo Scientific, Cat. #1550) were used for studies with the biotin mimic-tagged peptides. The rest of the procedure was formed identically to that described above except that tris-buffer saline, 0.1% BSA, 0.05% Tween-20 were used as the wash buffer instead of PBST, and the standard curve was constructed with whole molecule biotin conjugated to human IgG (Rockland, Cat, #009-0602) at concentrations of 2.5 to 10.0 ηg/ml.

Statistical Analysis. The correlation of CF antibody titers with ELISA results was estimated as the significance of the slope of the linear regression paired results as being non-zero.

Anti-coccidioidal antibody binding is restricted to $rCTS1_{111-310}$, but not to smaller rCTS truncations.

Figure 4:
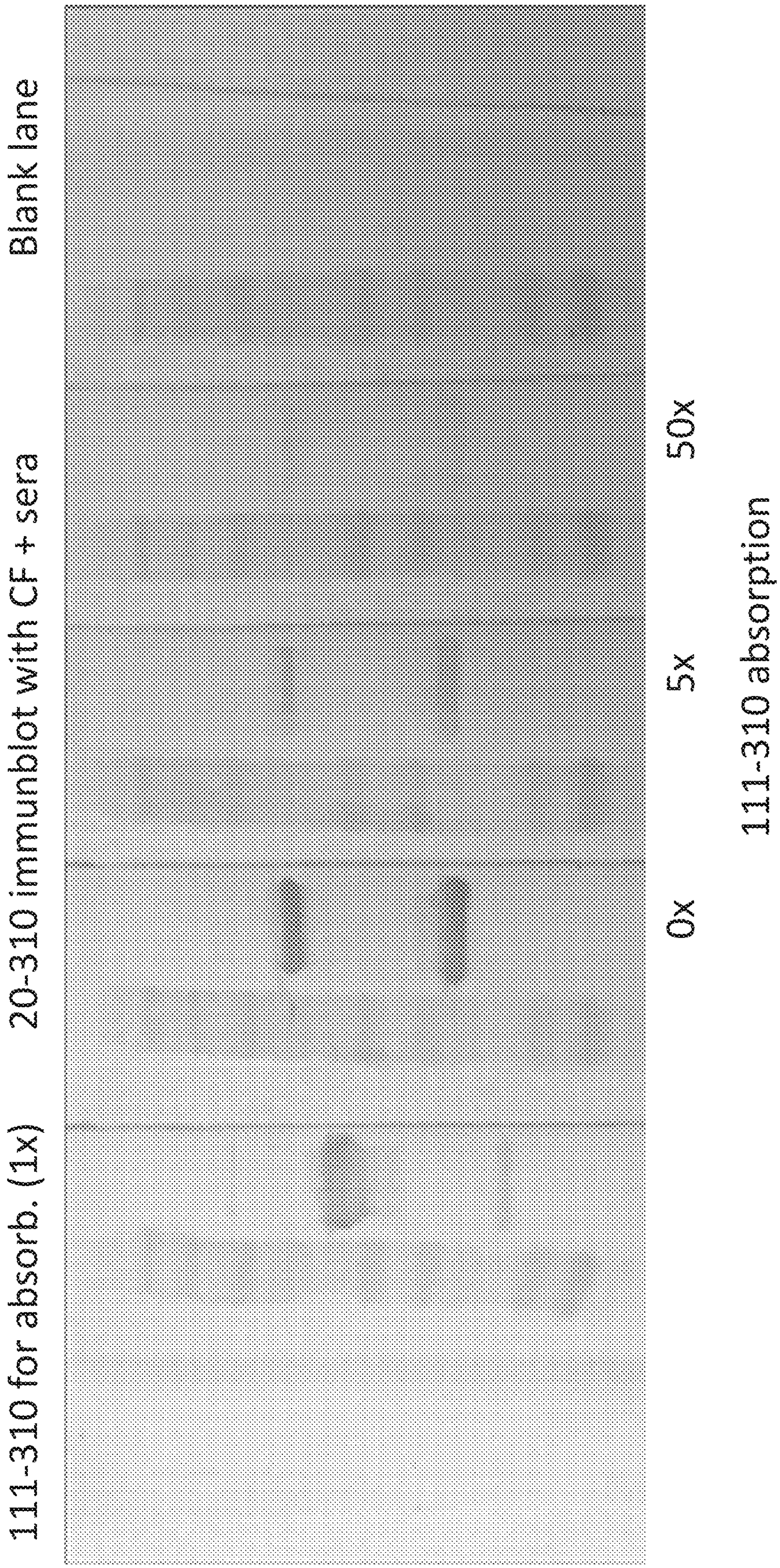
FIG. 4 shows the absorption of CF antibodies with increasing concentrations of $rCTS1_{111-310}$ (27.4 kDa) eliminates binding of CF antibodies to $rCTS1_{20-310}$ (34.7 kDa). The blank lane represents loading control.

Initial studies focused on the $rCTS1_{111-310}$ and compared it to $rCTS1_{20-310}$. As shown in FIGS. 1A-1B, the shorter truncation (27.4 kDa) demonstrates at least as much binding as the previously published $rCTS1_{20-310}$ (34.7 kDa). Further, adding increasing concentrations of $rCTS_{111-310}$ to antisera used to perform immunoblotting of $rCTS1_{20-310}$ virtually blocked all antibody binding to the membrane-bound peptide. This indicates that antibody binding to $rCTS1_{111-310}$ accounted for nearly all of the binding to $rCTS1_{20-310}$ (FIG. 4).

Figure 2:
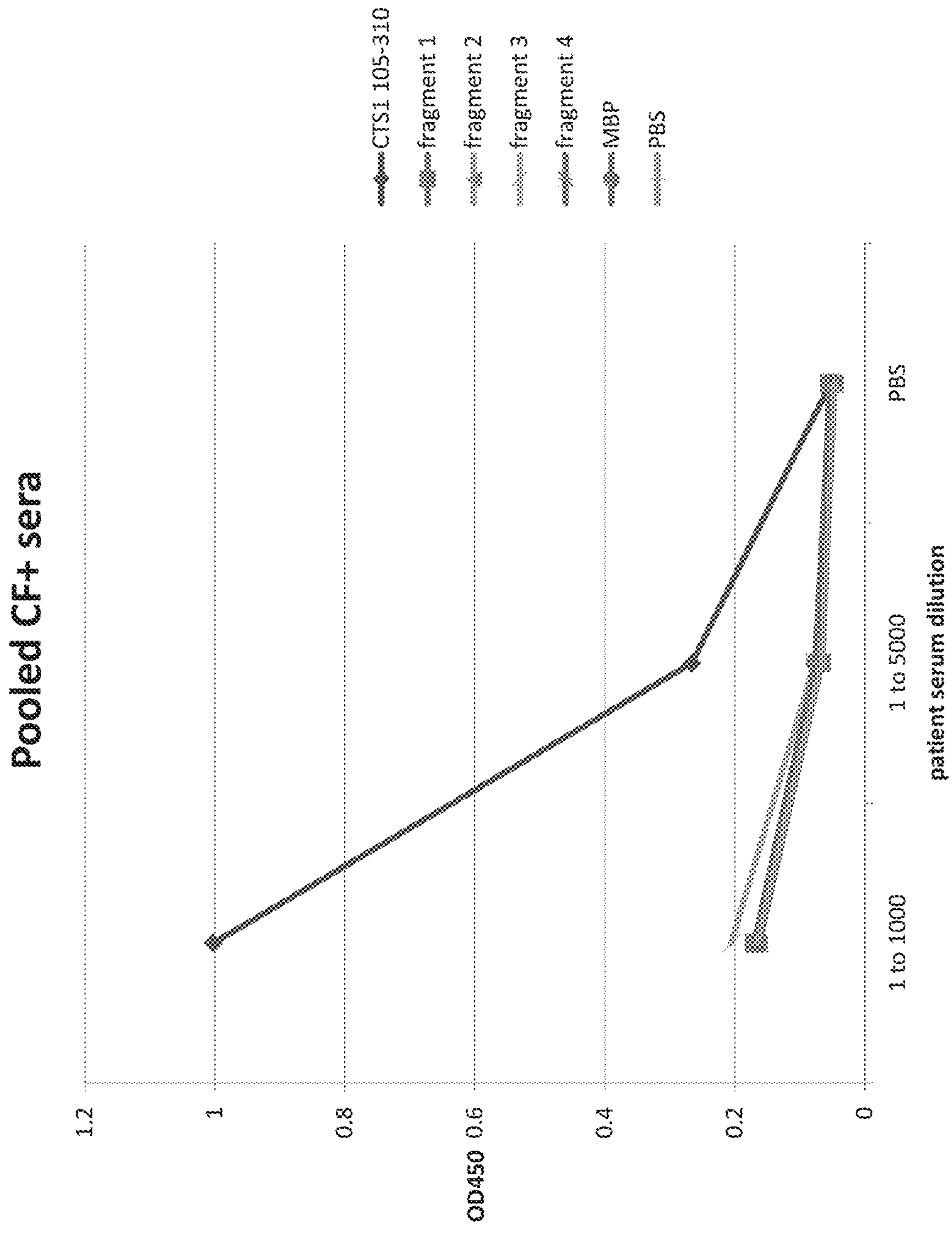

Next, four overlapping truncations ($rCTS1_{105-164}$, $rCTS1_{154-212}$, $rCTS1_{202-252}$, and $rCTS1_{240-310}$) were produced as shown in FIGS. 1A-1B. Each truncation overlapped by at least 11 residues. For these and future studies, $rCTS1_{105-310}$ (SEQ ID NO: 4; Table 1) was substituted for $rCTS1_{111-310}$ because this slightly larger truncation produced a several-fold greater yield of expression product and did not require denaturation and refolding to remain soluble. Of these truncations, only subunit #2 was soluble without MBP, and only subunit #3 ($rCTS1_{202-252}$) was soluble when the MBP was cleaved from the expression product. Of the four soluble truncations, western blots failed to show any significant binding to any of the subunits (FIGS. 5A & 5B). Also, comparing ELISA results when $rCTS1_{105-310}$ (SEQ ID NO: 4) or each of the four subunit peptides, or MBP alone, found virtually no binding by CF positive serum (FIG. 2). These unexpected findings suggested that most if not all of the binding of serum antibodies to $rCTS1_{105-310}$ was directed at conformational or discontinuous epitopes rather than epitopes of a primary amino acid sequence. Without wishing to limit the present invention to any theory or mechanism, it is believed that a similar assay may be used as a diagnostic test procedure.

Sensitivity and reproducibility of antibody binding to $rCTS_{105-310}$ is improved by tag-binding the peptide to the ELISA well.

Preliminary quantitative ELISA studies were performed using $rCTS1_{105-310}$ absorbed directly to plastic microtiter wells. However, day to day replication of binding of a pool created from CF antibody positive patient sera (CF titer of the pool was 1:8) resulted in unsatisfactory variability. Because the epitope mapping suggested that conformation of the peptide was critical, it was postulated that adhering the peptide directly to the plastic might result in steric distortion in an uncontrolled manner. Moreover, anchoring the antigen uniformly to the well by means of a terminal tag might result in the anchored antigen retaining its fluid phase conformation such as is the case in both classic CF antibody and immunodiffusion assays. To study this, an amino acid sequence mimic of biotin, SAWRHPQFGG (SEQ ID NO: 27), was cloned to the C-terminal of $rCTS1_{105-310}$. The biotin mimic sequence readily binds to streptavidin-coated plates to low μM affinity. Using this reconfigured assay, the quantitative ELISA results of replicates on 12 separate days ranged from 92 μg/ml to 174 μg/ml (average=112 μg/ml, sem±25).

Figure 3:
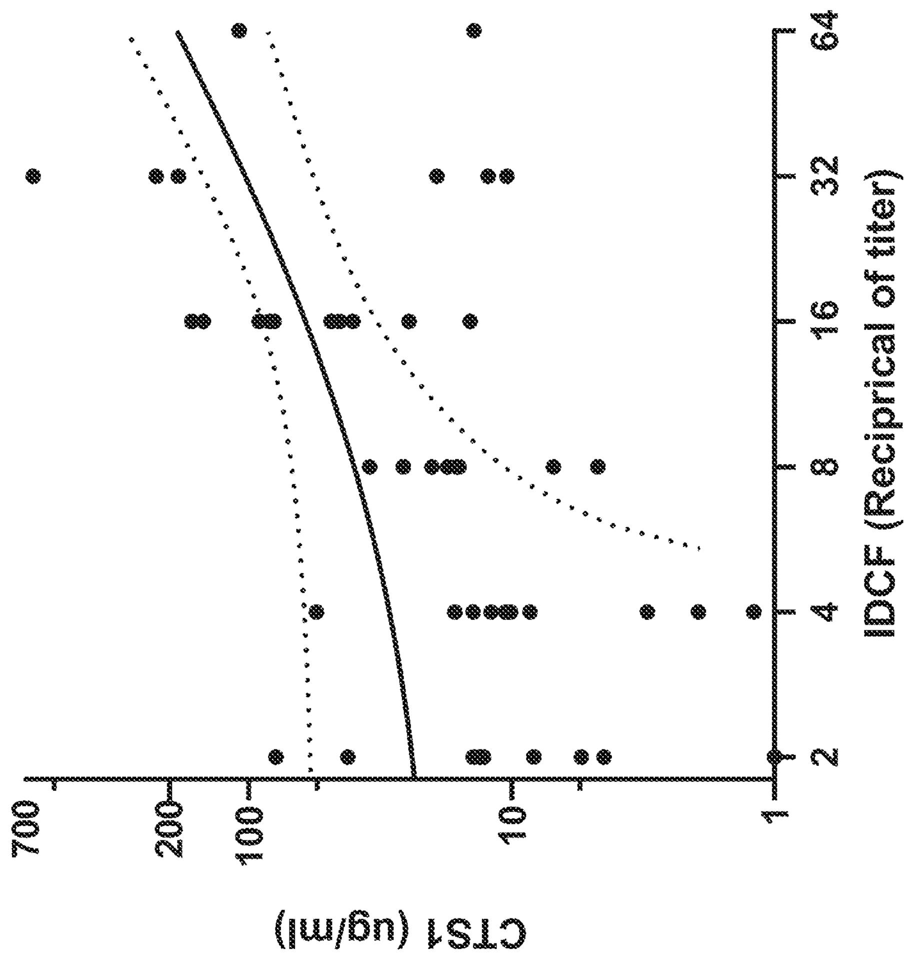
FIG. 3 shows the relationship of anti-$rCTS1_{105-310}$ antibody concentrations measured by ELISA to CF antibody titers for 50 individual human CF+ sera. The dotted lines represent the 95% confidence intervals for the slope of the regression line.

The quantitative antibody detection by ELISA performed was compared with $rCTS1_{105-310}$ absorbed directly to the well of uncoated plastic plates and with the biotin-mimic tag bound to streptavidin coated plates. As shown in Table 5, results with the mimic-tagged peptide uniformly detected more antibodies than did the peptide absorbed directly to the plastic with detection ratios ranging from 19- to 193-fold greater. Using the tag-bound $rCTS_{105-310}$ peptide, the 50 sera used to construct the serum pool individually were assayed, and the results are shown in FIG. 3. There is a significant relationship between the ELISA-measured anti-$rCTS1_{105-310}$ IgG concentration and the CF titer (p=0.0085) although the $r^2$ is only 0.14.

TABLE 3

Difference of results between quantitative ELISA results from 11 individual human sera using different methods of binding the antigen to the well of the plates.

| | Antibody binding (ug/ml) to $rCTS1_{105-310}$ | | |
|---|---|---|---|
| IDCF liter | Protein directly to the plastic | Protein with biotin mimic bound to Streptavidin-coated wells | Ratio of biotin mimic:plastic |
| 2 | 0.096 | 14.00 | 146 |
| 2 | 0.491 | 12.80 | 26 |
| 2 | 0.023 | 4.45 | 193 |
| 2 | 1.437 | 78.75 | 55 |
| 4 | 0.454 | 8.50 | 19 |
| 4 | 1.525 | 55.38 | 36 |
| 4 | 0.149 | 16.45 | 110 |
| 8 | 0.566 | 34.69 | 61 |
| 8 | 0.218 | 6.95 | 33 |
| 16 | 1.028 | 24.60 | 24 |
| 16 | 0.08 | 14.40 | 180 |
| | Average fold difference | | 79 |

The present absorption studies where $rCTS1_{111-310}$ was mixed with CF-positive serum virtually eliminated any binding to $rCTS1_{20-310}$ on the nitrocellulose membrane. However, none of four smaller, overlapping truncations of this region showed any appreciable antibody binding. The simplest explanation for this unexpected finding is that antibody binding to *Coccidioides*-specific epitope(s) depends upon conformation(s) present $CTS1_{111-310}$ that is lost with the individual smaller peptides. The expression of $rCTS1_{105-311}$ was found to be achieved in abundant quantities for serologic purposes.

Although the exact structure of the *Coccidioides*-specific conformational epitopes has not been identified, the present findings do suggest a possible reason why a recombinant CTS1 has not yet been used to develop an ELISA to mimic the quantitative CF antibody assay. An ELISA configuration with rCTS1 absorbed directly to the plastic well might well distort the protein's conformation in unpredictable ways and reduce its antibody binding. As found to be the case for $CTS1_{105-310}$ when compared to results with an ELISA where the peptide used a biotin-mimic tag sequence for oriented binding to streptavidin-coated wells (Table 3). Thus, using a biotin-mimic tag may offer a technical modification to improve a quantitative ELISA.

A general correlation between CF titer and ug/ml of antibody binding to $CTS1_{105-310}$ was observed (FIG. 3). The use of a standard curve to quantitate antibody binding has the advantage of allowing results from sequential specimens over time to be compared without running two specimens at the same time as has been recommended for optimal CF antibody titer comparisons. The correlation not being better than what was observed could be due to several factors. ELISA measures antibody binding to monomeric antigens which is influenced by the distribution of antibody avidities in different patient sera whereas CF antibody assays are based upon antigen-specific immune-complex formation. The relationship of these two dependencies is likely not uniform in different patients' sera. It is possible that better agreement between ELISA and CF results might be achieved using different conditions for antigen-antibody binding than those that were reused in the present studies. For example, if low-avidity antibodies in some specimens variably contributed to ELISA results, then adding urea might provide more stringency for antibodies binding to the plate and improve agreement.

The CF antibody assay titers have prognostic importance that was described in the 1950s. It should be noted that those pioneering studies were conducted by a single research laboratory, focused upon CM and before there were any effective therapies for this disease. Currently, CF antibody tests are provided for patient care by several reference laboratories. That antifungal therapy might alter the prognostic relationships noted earlier has recently been raised. The difference in individual sera between the present quantitative ELISA and CF antibody titers provides an opportunity in future studies to determine whether one or the other provide more precise prognostic information to clinicians.

Even if a quantitative ELISA is no more useful than CF antibody test results, it offers several practical advantages. ELISA is less complex than the CF test. ELISA reagents are readily available, and the format is familiar to most clinical laboratories. Also, ELISA is less labor intensive and can be automated. For all of these reasons, the present studies reported herein will provide further incentive for the development of a standardized quantitative ELISA as an alternative to the CF antibody assay.

The present invention describes isolated peptides of Cts1 that retain affinity for CF antibodies. These results help provide the basis for a reference enzyme-linked immunoassay to mimic quantitative results currently produced by the originally described CF antibody detection assay. FIG. 6 demonstrates that absorbance resulting from enzyme conjugate detection of antibodies is proportional to the CF titers. Therefore, measurement of absorbance of several different dilutions of a patient serum or other bodily fluid will result in absorbance curves that are proportional to the amount of CF antibody activity in the specimen. Using specimens of known CF antibody titers, a final protocol could determine the absorbance threshold at which the CF titer would correspond to a specific specimen dilution.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. An isolated Cts1 peptide having a sequence according to SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

2. An assay platform for detecting anti-coccidioidal antibodies, said platform comprising: (a) a solid support; and (b) an isolated Cts1 peptide having a sequence according to SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the Cts1 is peptide attached to the solid support.

* * * * *